(12) United States Patent
Lai et al.

(10) Patent No.: US 12,285,873 B2
(45) Date of Patent: *Apr. 29, 2025

(54) CLINICAL WORKFLOWS UTILIZING AUTONOMOUS AND SEMI-AUTONOMOUS TELEMEDICINE DEVICES

(71) Applicants: Teladoc Health, Inc., Purchase, NY (US); iRobot Corporation, Bedford, MA (US)

(72) Inventors: Fuji Lai, Goleta, CA (US); Timothy C. Wright, Santa Barbara, CA (US); Yair Lurie, Santa Barbara, CA (US); Yulun Wang, Goleta, CA (US)

(73) Assignees: Teladoc Health, Inc., Purchase, NY (US); iRobot Corporation, Bedford, MA (US)

( * ) Notice: Subject to any disclaimer, the term of this patent is extended or adjusted under 35 U.S.C. 154(b) by 242 days.

This patent is subject to a terminal disclaimer.

(21) Appl. No.: 17/954,155

(22) Filed: Sep. 27, 2022

(65) Prior Publication Data
US 2023/0016135 A1    Jan. 19, 2023

Related U.S. Application Data

(63) Continuation of application No. 16/807,017, filed on Mar. 2, 2020, now Pat. No. 11,453,126, which is a
(Continued)

(51) Int. Cl.
*G16H 40/67* (2018.01)
*B25J 9/16* (2006.01)
*G06Q 50/22* (2018.01)

(52) U.S. Cl.
CPC ............ *B25J 9/1676* (2013.01); *G06Q 50/22* (2013.01); *G16H 40/67* (2018.01); *Y10S 901/01* (2013.01); *Y10S 901/47* (2013.01); *Y10S 901/49* (2013.01)

(58) Field of Classification Search
None
See application file for complete search history.

(56) References Cited

U.S. PATENT DOCUMENTS

2006/0253300 A1* 11/2006 Somberg ................ G16H 40/67
600/300
2007/0129849 A1*  6/2007 Zini ..................... G05D 1/0225
700/258
(Continued)

OTHER PUBLICATIONS

Baldwin, G. (2011). Is telehealth finally ready to Answer the Call? Health Data Management, 19(4), 28-34. Retrieved from https://dialog.proquest.com/professional/docview/868333270?accountid=131444 (Year: 2011).*

*Primary Examiner* — Robert A Sorey
(74) *Attorney, Agent, or Firm* — Kory D. Christensen

(57) ABSTRACT

The present disclosure describes various clinical workflows and other methods that utilize a telemedicine device in a healthcare network. According to various embodiments, a healthcare practitioner may utilize a remote presence interfaces (RPIs) on a remote access device (RAD), such as a portable electronic device (PED) to interface with a telemedicine device. The healthcare practitioner may directly interface with a display interface of a telemedicine device or utilize the RPI on a RAD. The present disclosure provides various clinical workflows involving a telemedicine device to view patient data during a telepresence session, perform rounds to visit multiple patients, monitor a patient, allow for remote visitations by companions, and various other clinical workflow methods.

20 Claims, 23 Drawing Sheets

Related U.S. Application Data continuation of application No. 14/550,744, filed on Nov. 21, 2014, now Pat. No. 10,603,792, which is a continuation of application No. PCT/US2013/031708, filed on Mar. 14, 2013.

(60) Provisional application No. 61/766,623, filed on Feb. 19, 2013, provisional application No. 61/674,782, filed on Jul. 23, 2012, provisional application No. 61/674,796, filed on Jul. 23, 2012, provisional application No. 61/674,794, filed on Jul. 23, 2012, provisional application No. 61/650,205, filed on May 22, 2012.

(56) References Cited

U.S. PATENT DOCUMENTS

| | | | | |
|---|---|---|---|---|
| 2009/0089085 | A1* | 4/2009 | Schoenberg | G16H 40/20 705/2 |
| 2011/0288684 | A1* | 11/2011 | Farlow | B25J 19/023 901/1 |
| 2014/0009561 | A1* | 1/2014 | Sutherland | B62D 11/04 348/14.05 |
| 2015/0077502 | A1* | 3/2015 | Jordan | H04N 7/147 348/14.03 |

* cited by examiner

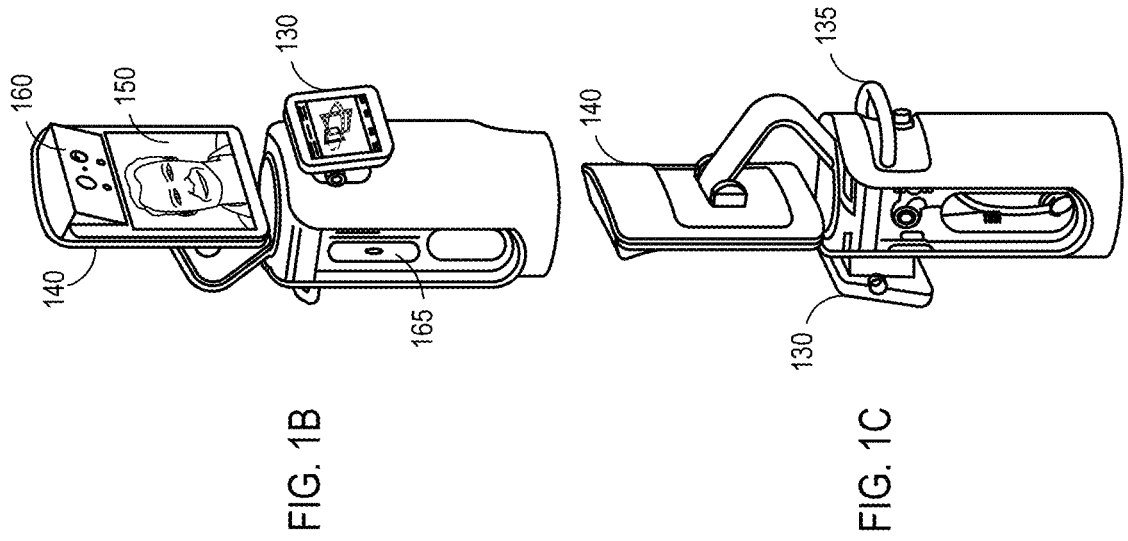
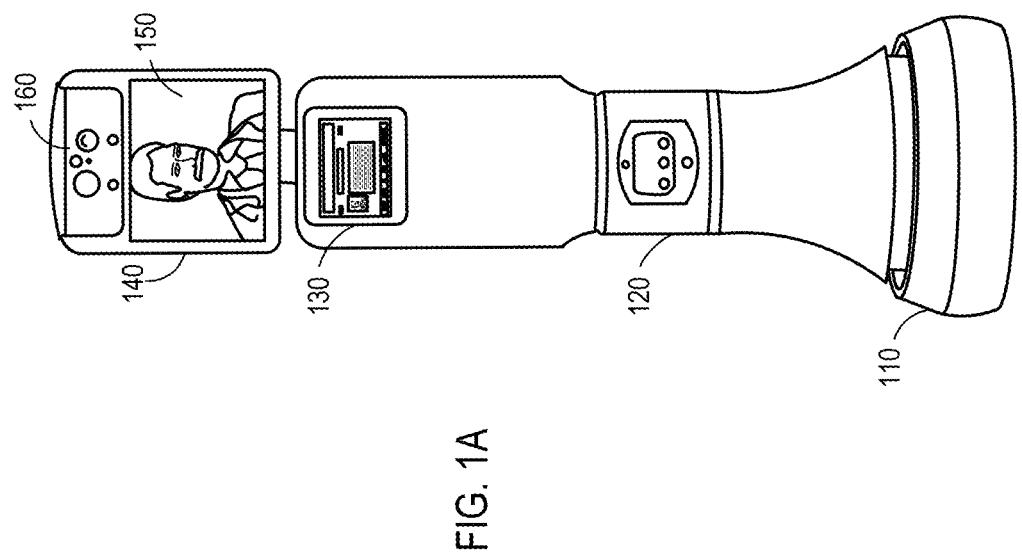

CLINICAL WORKFLOWS UTILIZING AUTONOMOUS AND SEMI-AUTONOMOUS TELEMEDICINE DEVICES

RELATED APPLICATIONS

This U.S. Patent Application is a continuation of U.S. patent application Ser. No. 16/807,017, filed Mar. 2, 2020, for CLINICAL WORKFLOWS UTILIZING AUTONOMOUS AND SEMI-AUTONOMOUS TELEMEDICINE DEVICES, which is a continuation of U.S. application Ser. No. 14/550,744 filed Nov. 21, 2014, which is a continuation of PCT Application No. PCT/US2013/031708 (the "PCT Application"), each of which is hereby incorporated by reference. These U.S. Patent Applications and the PCT Application also claim priority under 35 U.S.C. § 119(e) to: U.S. Provisional Application No. 61/650,205 filed May 22, 2012, titled "Remote Presence Interface and Patient Data Integration;" U.S. Provisional Application No. 61/674,794 filed Jul. 23, 2012, titled "Graphical User Interfaces Including Touchpad Driving Interfaces for Telemedicine Devices;" U.S. Provisional Application No. 61/674,796 filed Jul. 23, 2012, titled "Clinical Workflows Utilizing Autonomous and Semi-Autonomous Telemedicine Devices;" U.S. Provisional Application No. 61/674,782 filed Jul. 23, 2012, titled "Behavioral Rules For a Telemedicine Robot To Comply With Social Protocols;" U.S. Provisional Application No. 61/766,623 filed Feb. 19, 2013, titled "Graphical User Interfaces Including Touchpad Driving Interfaces for Telemedicine Devices;" which applications are hereby incorporated by reference in their entireties.

TECHNICAL FIELD

This disclosure relates to clinical workflows involving autonomous and semi-autonomous robotic devices. More specifically, this disclosure relates to clinical workflows for telemedicine devices in a healthcare facility.

BRIEF DESCRIPTION OF THE DRAWINGS

FIGS. 1A-C illustrate example embodiments of a telepresence device.

Figure 2B:
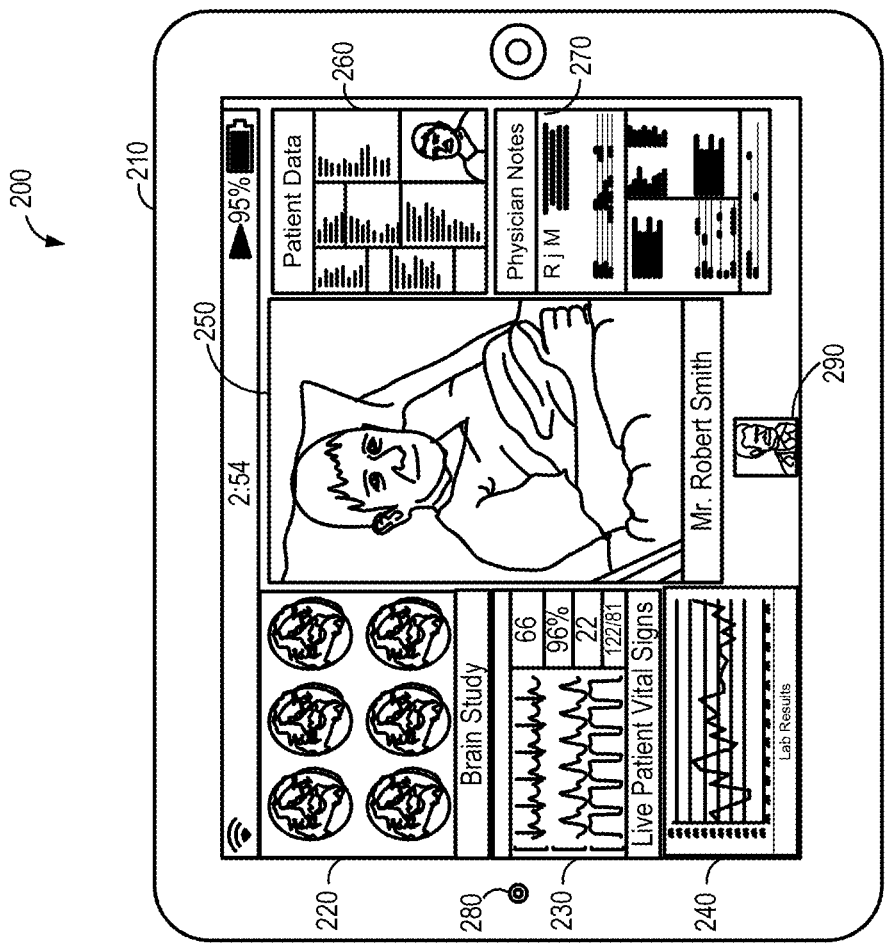
FIGS. 2A and 2B illustrate embodiments of what may be displayed during a consult on a telepresence device and via an RPI on a PED, respectively.

The described features, structures, and/or characteristics of the systems and methods described herein may be combined in any suitable manner in one or more alternative embodiments, and may differ from the illustrated embodiments.

DETAILED DESCRIPTION

Healthcare facilities may include telemedicine technologies, such as telepresence and/or telemedicine devices in a telepresence network that allow remote healthcare practitioners to provide services to patients and/or other healthcare practitioners in remote locations. For example, a remote healthcare practitioner may be a neurologist practicing in a relatively large hospital who may, via a telemedicine device, provide services and consultations to patients and/or other medical professionals in a relatively small hospital that may not otherwise have a neurologist on staff.

The present disclosure provides various methods and clinical workflows that utilize autonomous, semi-autonomous, and/or manually controlled telemedicine devices to improve at least one aspect of healthcare. As used herein, a telepresence device may broadly allow for remote video and/or audio connections between a remote user and a local patient. A telemedicine device may be a type of telepresence device configured with one or more additional characteristics or features for use in a healthcare facility. A telemedicine device may be autonomous, semi-autonomous, and/or manually controlled.

In a remote presence (RP) system, a telemedicine device, such as an autonomous robot, a semi-autonomous robot, a stationary system, a mobile system, and/or a stationary system mounted to a mobile cart may communicate with an interfacing device via a communications network. In various embodiments, a remote access device (RAD) may be used to view a remote presence interface (RPI), an application running on the RAD. A remote user may utilize the RPI on any of a wide variety of electronic devices, including computers, tablets, cellular phones, various portable electronic devices (PEDs), and/or other suitable electronic devices (referred to as RADs throughout).

A user may select one or more endpoint telepresence devices via the RPI. Once a secure connection is established between the telepresence device and the RAD, the RPI, being displayed on the RAD, may include a video feed from the telepresence device. In addition, the RPI may include any number of navigational panels, setting controls, telemetry data, map views, and/or patient information, some of which are described in detail herein.

In some embodiments, the RPI may allow a user to select a control mode for the telepresence device. The telepresence device may be controlled manually by the user, operate semi-autonomously, or operate autonomously based on the control mode selected by the user. As described herein, the RPI may allow a user to specify movement (i.e., a location within a healthcare facility or a physical movement, such as a head turn) of the telepresence device using a destination selection panel, an arrow, a physical or virtual joystick, a touch pad, click-to-destination, and/or other navigational control.

The RPI may provide various notifications associated with the network connection, the user's remote device, a patient, a healthcare facility, a healthcare practitioner, a telepresence device, and/or the like. The RPI may include a media management module configured to allow a user to record and/or store audio and/or visual data for subsequent use. A settings panel may allow settings on the RAD and/or the telepresence device to be adjusted. In some views, multiple windows may provide quick access to various panels of information. For example, one or more panels associated with a video feed, patient data, calendars, date, time, telemetry data, telepresence device data, healthcare facility information, healthcare practitioner information, menu tabs, settings controls, and/or other features described herein may be displayed simultaneously and/or alone in a full-screen mode.

The RPI may utilize a camera of the user's device to capture an image of the user and display the image on a display of the telepresence device. In some embodiments, the image on the display of the telepresence device may be modified and/or enhanced. In various embodiments, multiple healthcare practitioners may participate in a remote consultation.

The RPI may incorporate sub-applications and/or provide access to related applications, such as a StrokeRESPOND application configured to provide one or more functions and/or workflow processes described in U.S. patent application Ser. No. 12/362,454, titled "DOCUMENTATION THROUGH A REMOTE PRESENCE ROBOT," filed on Jan. 29, 2009, which application is hereby incorporated by reference in its entirety.

The RPI may be configured to maintain a "stateful" connection at the application layer, such that the session and variables may be maintained in the event that the connection is lost or dropped. The RPI may then attempt to re-establish the session using these variables when the connection is restored. The RAD and/or RPI may have settings that enable a user to maximize frame rate or image quality at the expense of the battery life of the device, or vice versa.

According to one embodiment, the RPI may include a "dashboard" configured to allow a healthcare practitioner to visualize patient data during a telepresence session. The patient data may be intelligently populated on a remote presence interface (RPI) of a remote access device (RAD) used by the healthcare practitioner during the remote telepresence session. The dashboard of patient data may be automatically populated based on the patient, context, and/or other factors.

A telepresence network and/or device may detect that a patient's data is being reviewed by the physician and the telepresence device may be automatically dispatched to the patient's room. Accordingly, when the physician remotely connects to the telepresence device, the telepresence device may already be at the patient's bedside or en route to the patient's bedside. In one embodiment, the telepresence device may perform patient rounds, checking on and/or recording information for a plurality of patients at scheduled intervals. The healthcare practitioner may review patient data recorded during the rounds.

In some embodiments, the healthcare practitioner may use a multimedia module of the RPI to save waveforms or other patient data of interest. The healthcare practitioner may share historical waveforms or other patient data with a bedside team directly via the RPI, via a multi-person telepresence session, and/or via access to a multimedia database. Additionally, the telepresence device may observe and/or record anomalous activity of a patient during an observation period.

In some embodiments, the telemedicine device may track the amount of time it is utilized for each particular patient, and/or the type of use for each patient. For example, each encounter with a patient may be categorized by type of visit, the type of person making the visit, the outcome of the visit, the reason for the visit, or other characteristic of the visit. In some embodiments, a telemedicine device may intelligently facilitate remote telepresence connections, such as automatically requesting the assigned doctor for a particular patient when the patient requests "a doctor."

In some embodiments, the telemedicine device may facilitate communication with an electronic medical record database to automatically (or via manual instructions) update an electronic medical record via the telemedicine device and/or via an RPI on a RAD. In some embodiments, a telemedicine device may allow a companion of a patient to perform remote visits. For example, a spouse, friend, family member, domestic partner, and/or the like may remotely access a telemedicine device to initiate a telepresence session with a patient.

Reference throughout this specification to "one embodiment" or "an embodiment" means that a particular feature, structure, or characteristic described in connection with the embodiment is included in at least one embodiment. Thus, the appearances of the phrases "in one embodiment" and "in an embodiment" in various places throughout this specification are not necessarily all referring to the same embodiment. In particular, an "embodiment" may be a system, an article of manufacture (such as a computer-readable storage medium), a method, and/or a product of a process.

The phrases "connected to" and "in communication with" refer to any form of interaction between two or more entities, including mechanical, electrical, magnetic, and electromagnetic interaction. Two components may be connected to each other even though they are not in direct contact with each other and even though there may be intermediary devices between the two components.

Types of telepresence devices include, but are not limited to, remote telepresence devices, mobile telepresence units, and/or control stations. For example, a remote telepresence device may include a telepresence robot configured to move within a medical facility and provide a means for a remote practitioner to perform remote consultations. Again, a telemedicine device, as used herein, may refer to any type of telepresence device having one or more additional features or characteristics for use in a healthcare capacity. Telepresence devices may comprise any of a wide variety of endpoint devices, such as those described in U.S. patent application Ser. No. 13/360,579 filed on Jan. 27, 2012, titled "INTERFACING WITH A MOBILE TELEPRESENCE ROBOT," and U.S. patent application Ser. No. 13/360,590 filed on Jan. 27, 2012, titled "INTERFACING WITH A MOBILE TELEPRESENCE ROBOT," which applications are hereby incorporated by reference in their entirety.

The term "remote access device" (RAD) as used throughout the specification may include any of a wide variety of electronic devices, including portable electronic devices (PEDs). Specifically contemplated and illustrated are tablet-style electronic devices, including, but not limited to, electronic readers, tablet computers, tablet PCs, cellular phones, interactive displays, video displays, touch screens, touch computers, and the like. Examples of PEDs include the Apple iPad®, iPod®, and iPhone®, the Hewlett Packard Slate®, the Blackberry Playbook®, the Acer Iconia Tab®, the Samsung Galaxy®, the LG Optimus G-Slate®, the Motorola Xoom®, the HP touchpad Topaz®, the Dell Streak®, and the like. Additionally, a RAD may include a workstation, a desktop, a stationary monitor, and/or other non-portable electronic device. Throughout this description and the accompanying drawings, a tablet-style touch-screen PED is used as an illustrative RAD, however, any of a wide variety of RADs and/or other electronic devices may be used instead.

The described features, operations, or characteristics may be combined in any suitable manner in one or more embodiments. The order of the steps or actions of the methods described in connection with the embodiments disclosed may be varied. Moreover, one or more steps may be omitted from a method, and/or steps from one or more methods may be combined. Thus, any order in the drawings or Detailed Description is for illustrative purposes only and is not meant to imply a required order, unless otherwise specified.

In various embodiments, the techniques introduced herein may be embodied in machine-executable instructions executed by a general-purpose or special-purpose computer (or other electronic device). Alternatively, the techniques may be performed by hardware components that include specific logic for performing the steps, or by a combination of hardware, software, and/or firmware. Accordingly, the various components, modules, systems, and/or features described herein may be embodied as modules within a system. Such a system may be implemented in software, firmware, hardware, and/or physical infrastructure.

In other embodiments, the techniques may also be embodied as a computer program product, including a non-transitory machine-readable medium having stored thereon instructions that may be used to program or be executed on a computer (or other electronic device, such as a PED) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable media suitable for storing electronic instructions.

The various embodiments disclosed herein will be best understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations and/or components are not shown or described in detail.

FIGS. 1A-C illustrate example embodiments of a telepresence device configured to function as a telemedicine device. As illustrated in each of FIGS. 1A-C, a telepresence device may comprise a base 110 including navigation components configured such that the telepresence device is capable of being manually driven, semi-autonomously driven, and/or autonomously driven. Various display features, connection features, and/or data ports 120, 130, and 165 may be available on a mid-section of the telepresence device. The telepresence device may also include a handle 135. A head portion 140 of the telepresence device may include one or more cameras 160, speakers, and/or microphones. Multiple cameras 160 may be useful to render 3D images, and multiple microphones and/or speakers may be useful for rendering and/or generating directional sound. The head portion may also include a display 150 configured to display an image captured using an RPI on a RAD. The head portion may be configured to rotate, pan, and/or tilt, independent of the base portion 110.

The display 150 and/or the interface 130 may comprise a touch screen or other interface to receive inputs. In some embodiments, if the telepresence device is an autonomous mobile telepresence device, the display 150 and/or the interface 130 may provide a list of destinations or patients that, as described herein, can be selected to send the telepresence device to the selected destination or location. The display 150 and/or the interface 130 may also enable a person to stop the telepresence device when it is autonomously navigating, and likewise enable the telepresence device to resume autonomous navigation to its destination. The display 150 and/or the interface 130 may additionally have a button or menu option that instructs the telepresence device to autonomously navigate to a dock or charging station. The display 150 and/or the interface 130 may include buttons or menu options for various settings, or to page or notify support personnel of a problem with, or question regarding, the operation of the telepresence device.

Figure 2A:
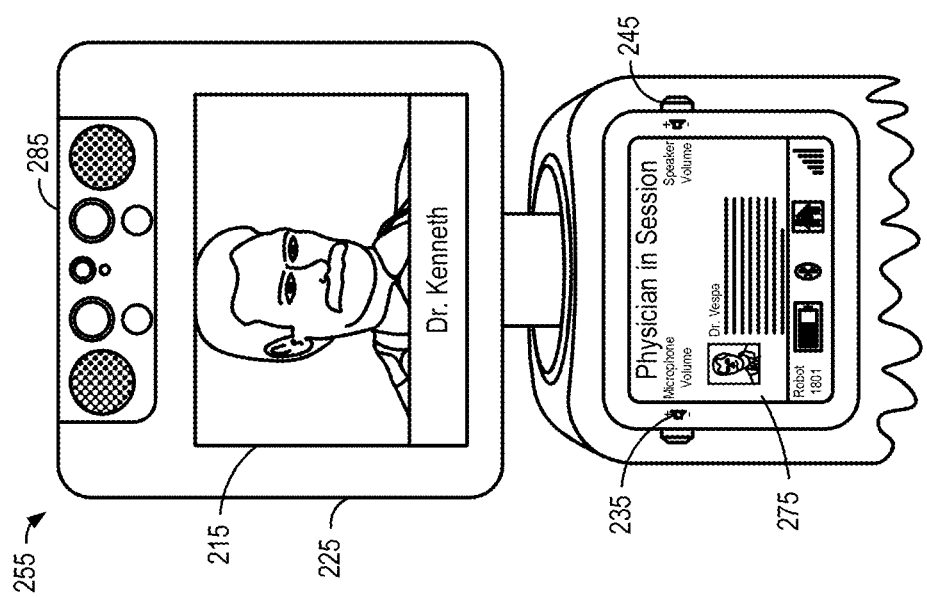

FIGS. 2A and 2B illustrate an embodiment 200 of what may be displayed during a consult on a telepresence device 255 and via an RPI on a PED 210, respectively. As illustrated, the telepresence device 255 may include audio and/or visual equipment 285 to capture images and/or audio for display on the PED 210. PED 210 may include a camera 280 to capture an image 290 for display on a screen 215 of a head portion 225 of the telepresence device 255. In addition to or in place of the image 290, the screen 215 may display a user interface for and/or information associated with an application running on the telepresence device. In some embodiments, the image 290 of a remote healthcare practitioner may be reduced in size or eliminated to accommodate the display of the user interface and/or other information on the screen 215, or the user interface and/or additional information may be displayed as an overlay on the image 290.

A lower portion of the telepresence device may include adjustment knobs 235 and 245. In some embodiments, and as illustrated, the adjustment knobs 235 and 245 may be used for controlling the microphone volume 235 and/or the speaker volume 245. Additionally, a screen 275 may provide additional information and/or provide controls for the telepresence device 255. For example, the screen 275 may provide additional information about the user of the PED 210. For instance, a patient being cared for via the telepresence device 255 may see a healthcare practitioner using the RPI on the PED 210. Similarly, the healthcare provider may see and interact with the patient via the telepresence device 255 using the RPI on the PED 210.

The screen 275 may be a touch screen device and provide an interface for initiating, stopping, interrupting, and/or otherwise controlling any of the various methods, workflows, and/or operations described herein. Additionally or alternatively, the screen 275 may provide an interface for patients and/or healthcare practitioners to provide information associated with any of the methods, workflows and/or operations described herein. According to various embodiments, the screen 275 may receive inputs and/or otherwise be controlled by a remote interface, a touch screen display, one or more integrated or connected peripheral devices (e.g., keyboard, mouse, buttons), and/or via adjustment knobs 235 and 245. For example, adjustment knobs 235 and 245 may be used to navigate and/or select menus features, displayed content/pages, and/or icons on the screen 275 and/or screen 215.

The RPI on a PED 210 illustrates multiple panels. As illustrated, a radiography panel 220 may display images associated with a patient displayed in a live video feed 250. Telemetry data 230, lab results 240, patient data 260, and physician notes 270 may be displayed in various other panels on PED 210 via the RPI. According to various embodiments, each of the panels 220, 230, 240, 250, 260, 270, and 290 may be moved, enlarged, merged with another panel, removed, and/or captured (recorded), intelligently based on decisions made by the RPI, based on usage history, based on relevancy, and/or based on user selection. Camera 280 may be selectively enabled or disabled by the user.

The RPI may enable complete integration of patient data monitoring with the remote telepresence session, thereby adding a dimension of data-driven functionality uniquely valuable in telemedicine applications. The user may select an icon from a toolbar or other panel to activate a patient bedside data monitoring app, such as those offered by any of a variety of real-time patient data monitoring application providers. Upon selecting the appropriate icon, a patient data monitoring window may appear in the RPI. The user may expand this pane to a full screen view, reposition the pane, and/or resize the pane as described above. The RPI may show any number of real-time or archived patient biometrics or waveforms, such as temperature, heart rate, pulse, blood pressure, oxygen saturation, or the like.

Using the touch-screen interface, the user may pause and resume real-time, time-delayed, or archived patient data. The user may move back and forth through time-based patient data using dragging or swiping gestures, or the user may zoom or scale the waveform or metric along an amplitude axis and/or time axis. The application may further allow the user to set markers along a waveform to measure variations in amplitude or time associated with various features of the patient data, such as peaks, valleys, maxima or minima (global or local), global averages, running averages, threshold crossings, or the like.

The data may be collected from bedside monitors or other monitoring devices in real-time and archived for a period of time (or indefinitely) in a server or database. The monitoring app may be a separate application and/or integrated within the RPI. The monitoring app may retrieve the relevant data and provide it to the RPI through an application programming interface (API) and/or the RPI may independently retrieve the data from a database.

The data may also be collected by a data collection components of the telepresence device by, for example, directing a camera of the telepresence device to the display of a monitoring device, and either recording video of the monitor display or performing image analysis on the video image to extract the patient data. The user and/or telepresence device may annotate the data and store the annotations with the data, either locally or in a remote server, for later retrieval. The monitoring app may enable alarms, alerts, notifications, or other actions or scripted activities set to take place in response to certain events in the data.

In some embodiments, if a patient's vitals or other biometrics trigger an alert or alarm condition, the telepresence device may be configured to autonomously navigate to the bed or room number of that patient, and send a notification or invitation to a doctor, caregiver, or specialist to begin a telepresence session with the patient. Additionally, when a healthcare practitioner initiates a session with a telepresence device and selects either a location or destination or patient to visit with the autonomous telepresence device, the bedside or biometric data for a patient associated with the selected location, destination, or name may be automatically retrieved and used to populate a "dashboard" of patient data that the healthcare practitioner can then review, annotate, or otherwise interact with as discussed above.

Moreover, an autonomous mobile telepresence device may be used to conduct patient rounds in a healthcare facility. As the telepresence device moves from one location to the next, the location of the telepresence device may be used to retrieve the name of a patient associated with that location, and that patient's biometric, bedside data, and/or other patient data may be retrieved and used to populate a patient dashboard on a display of the PED.

In addition, an autonomous mobile telepresence device may be scripted or scheduled to make scheduled stops at various beds, rooms, locations, or patients associated therewith. The RPI may retrieve the names or contact info of people (such as doctors, nurses, students, family members, etc.) associated with a scheduled or upcoming stop at a particular patient or location, and send a notification via SMS, email, etc., to the associated people inviting them to join the telepresence session by receiving audio and/or video from the session on a PED via the RPI. To accommodate a time interval that may be necessary or convenient to allow others to join the session, the telepresence device may send invitations, notifications, and/or reminders to join the session a predetermined amount of time prior to the time the session is scheduled to begin. Repeated or reminder notifications may be sent to each party at regular or decreasing intervals to remind them of an upcoming session. The notifications may contain a hyperlink to follow to join the session, a link to the RPI, an app notification or badge for display on the PED, or the address or phone number of another device address to connect to. The notification may further include a username, password, pin and/or other credential(s) that the invitees must provide to join the session.

Figure 3:
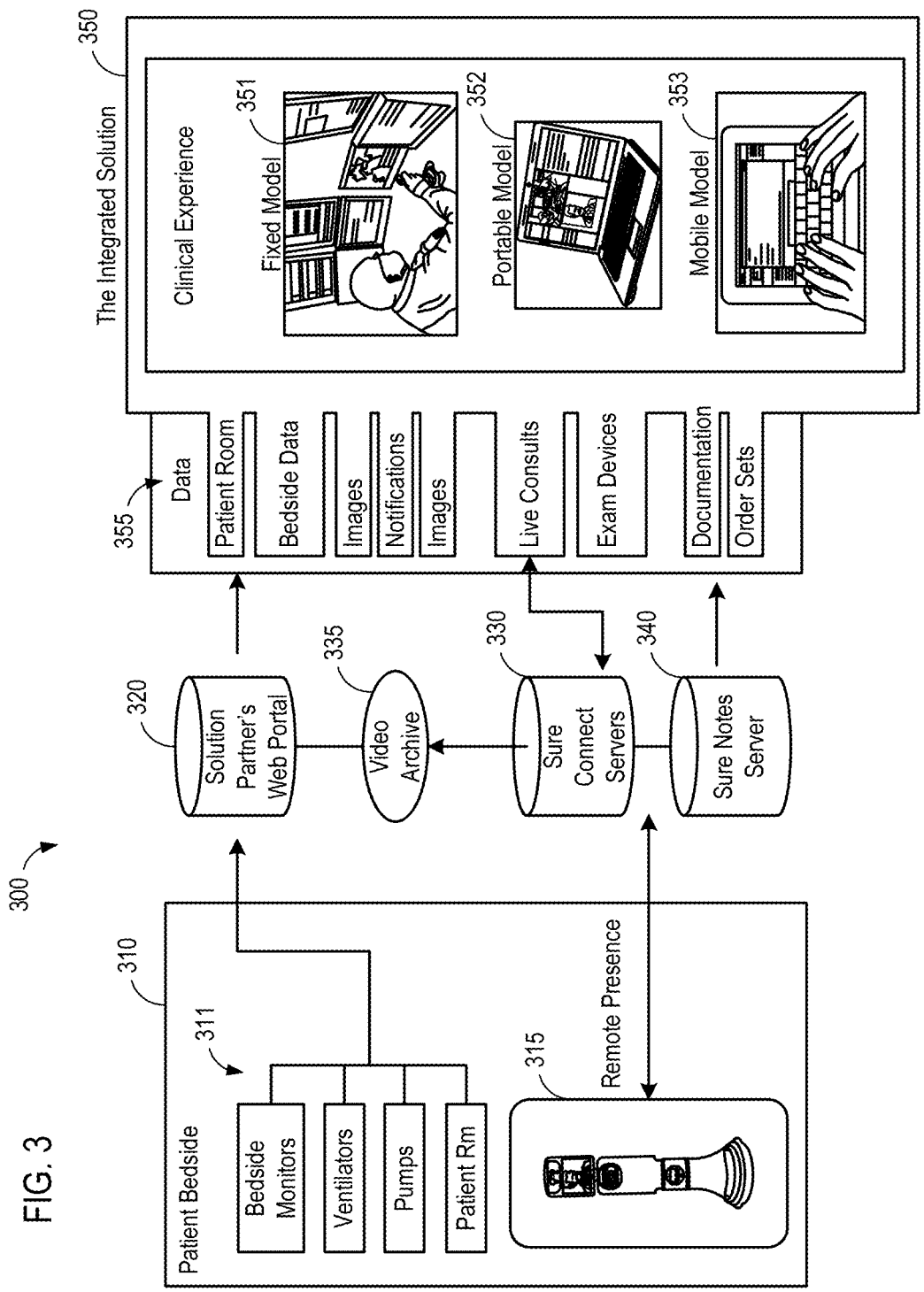
FIG. 3 illustrates a flow diagram of data between telemedicine devices and remote user devices.

FIG. 3 illustrates a flow diagram 300 of data between telemedicine devices and remote user devices. As illustrated, at a patient bedside 310, various patient data may be collected via bedside monitors, ventilators, pumps, data such as the patient room number, and other patient data, at 311. The various patient data may be securely available via a solution partner's web portal 320. A telemedicine device 315 may perform any of the various services provided herein and include communication components (e.g., wired and/or wireless network components) to interface with one or more servers 330 and 340, directly with a RAD, or with other telepresence devices. Video archives 335 may be shared or communicated between the servers 330 and 340 and the solution partner's web portal.

The various data and services collected at the patient bedside 310 may be made available via the web portal 320 and/or the servers 330 and 340. The data, such as patient room information, bedside data, images, notifications, images, live consults, exam devices, documentation, orders sets, and the like, may be available useable via one or more clinical experiences 350. For example, the data may be made available via a fixed RAD 351, a portable RAD (PED) 352, and/or on mobile devices (PEDs) 353.

Figure 4:
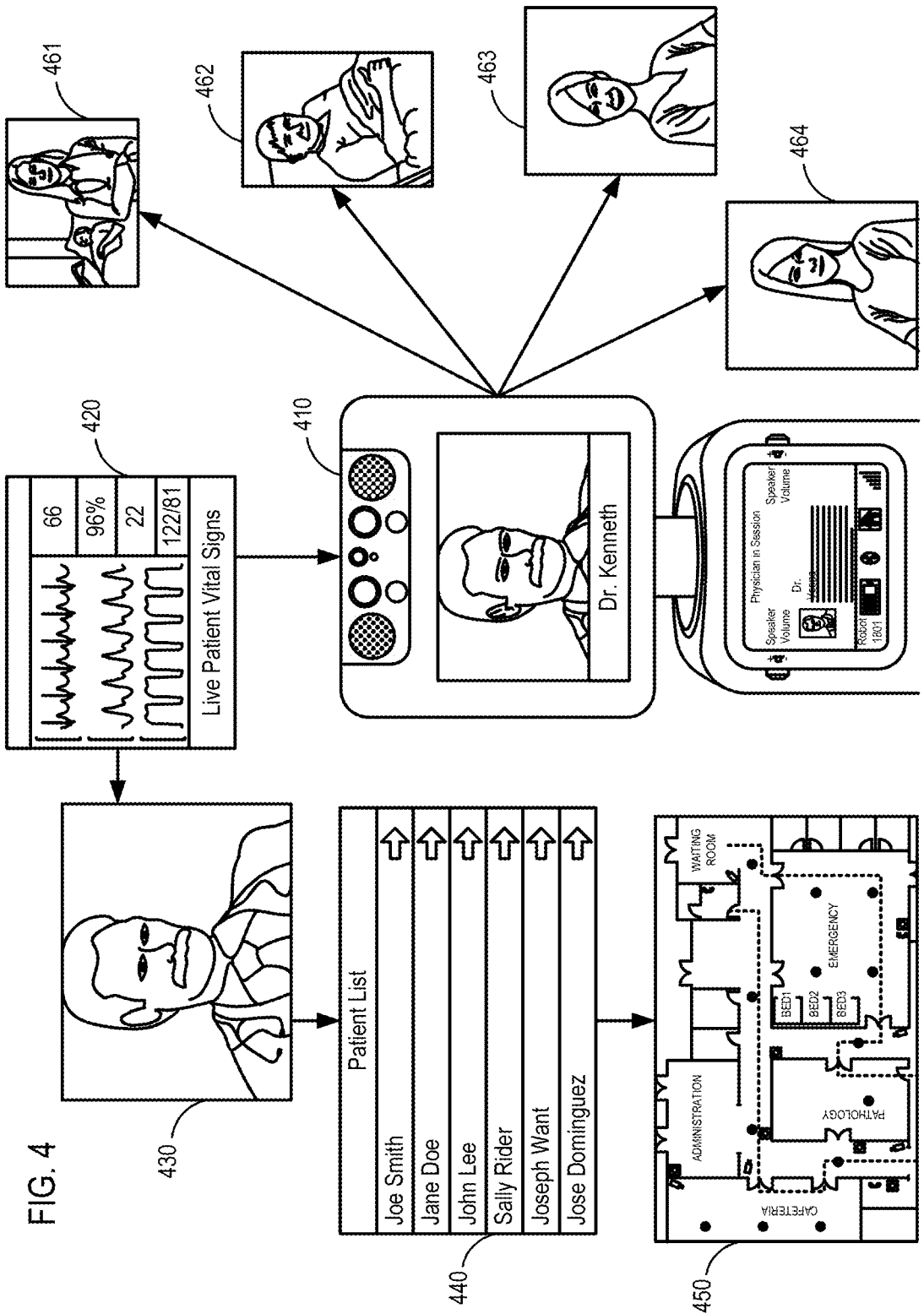
FIG. 4 illustrates various remote features available to a healthcare practitioner using a telemedicine device.

FIG. 4 illustrates various remote features available to a healthcare practitioner 430 using a telemedicine device 410. As illustrated, a telemedicine device 410 may allow a healthcare practitioner 430 to participate in telepresence communication sessions with various patients 461 and 462 and/or other healthcare practitioners 463 and 464. Additionally, the telemedicine device 410 may allow a healthcare practitioner 430 to view telemetry data 420, switch between and autonomously navigate to various patients on a patient list 440, and/or navigate within a healthcare facility using a plan view map 450. In various embodiments, the telemedicine device may be configured to autonomously and/or semi-autonomously navigate with a healthcare facility.

Figure 5:
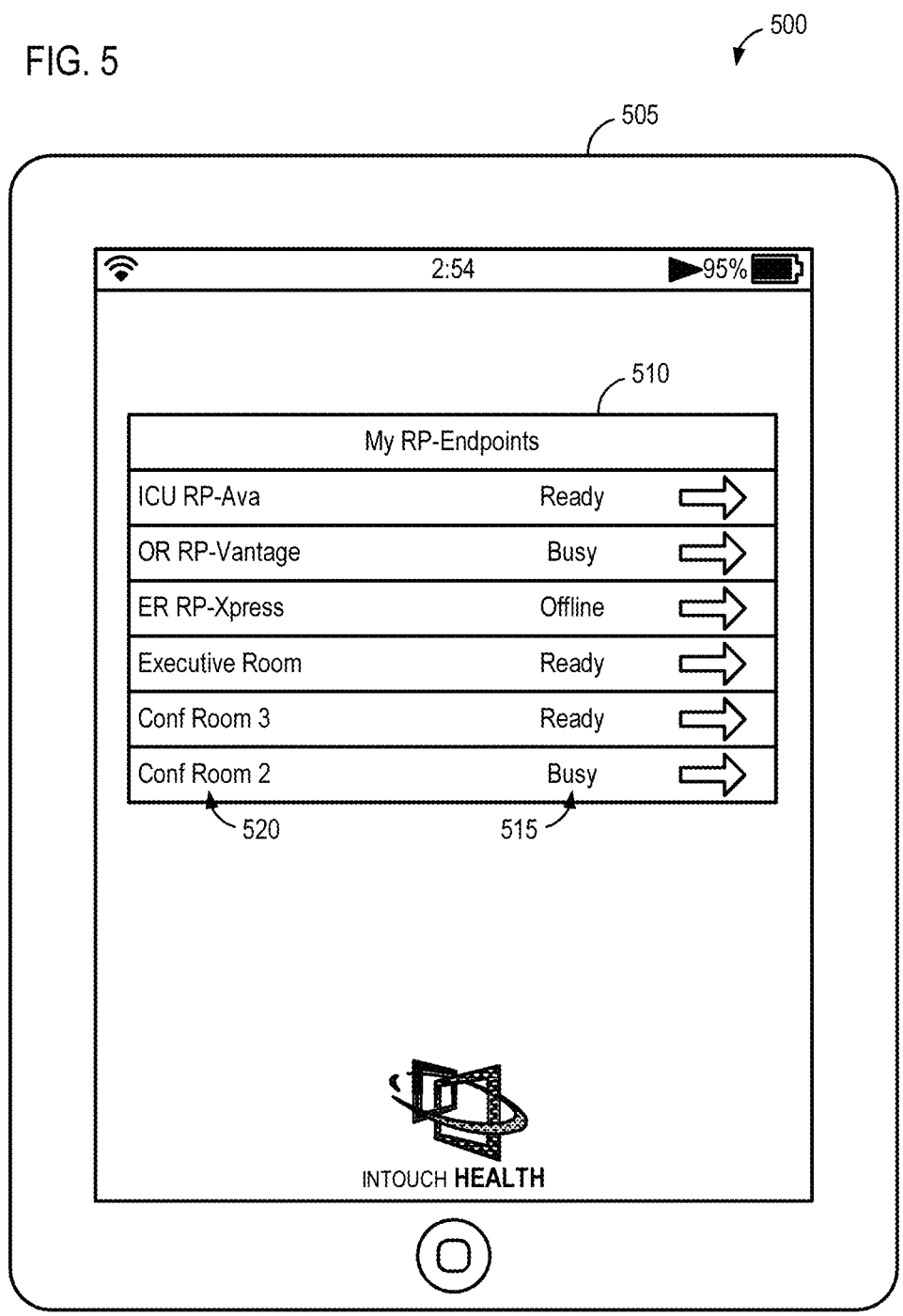
FIG. 5 illustrates an embodiment of an endpoint list of various telepresence devices and their connectivity state.

FIG. 5 illustrates an embodiment 500 of an endpoint list 510 generated by the RPI running on a RAD 505. The endpoint list 510 may include various telepresence devices 520 and their respective connectivity states 515. A user may indicate (via a touch, a click, using a stylus, and/or by speaking) to which of the available endpoints he or she would like to connect. Where an ADT (Admissions, Discharges, and Transfers) data source is available, patients may also be listed. Selecting a particular patient may initiate a connection to an endpoint device that is assigned to, associated with, or otherwise in proximity to the selected patient. A device in proximity to the patient could be a device nearest a location of the selected patient, the same bed, room, or floor number.

The list may also include doctors, nurses, staff, or any other persons that may currently (or for a scheduled period of time) be associated with a particular location to which the endpoint can navigate. The list of available endpoints may be searchable and/or filterable. In some embodiments, the list may be implemented with a text box in the window, together with the list of endpoints, in a separate window, or in separate tabs. As the user enters alphanumeric characters into the text box, the list may be instantaneously filtered to exclude endpoints whose names do not match the character string currently contained in the text box. Other filtering parameters may be specified, such as endpoint type, manufacturer, status, facility, building, floor, room, customer, or any other grouping. Logical, arbitrary, or otherwise customized groupings of endpoints may be created by a user or administrator, and these groupings may additionally be used to filter or otherwise search the list of endpoints.

Each endpoint in the list may have an associated status indicator, which informs the user whether a device is ready, busy, offline, in a private session, in a multi-presence session (which the user may join to receive session audio, video, images, or potentially control some or all functions of the endpoint).

Figure 6:
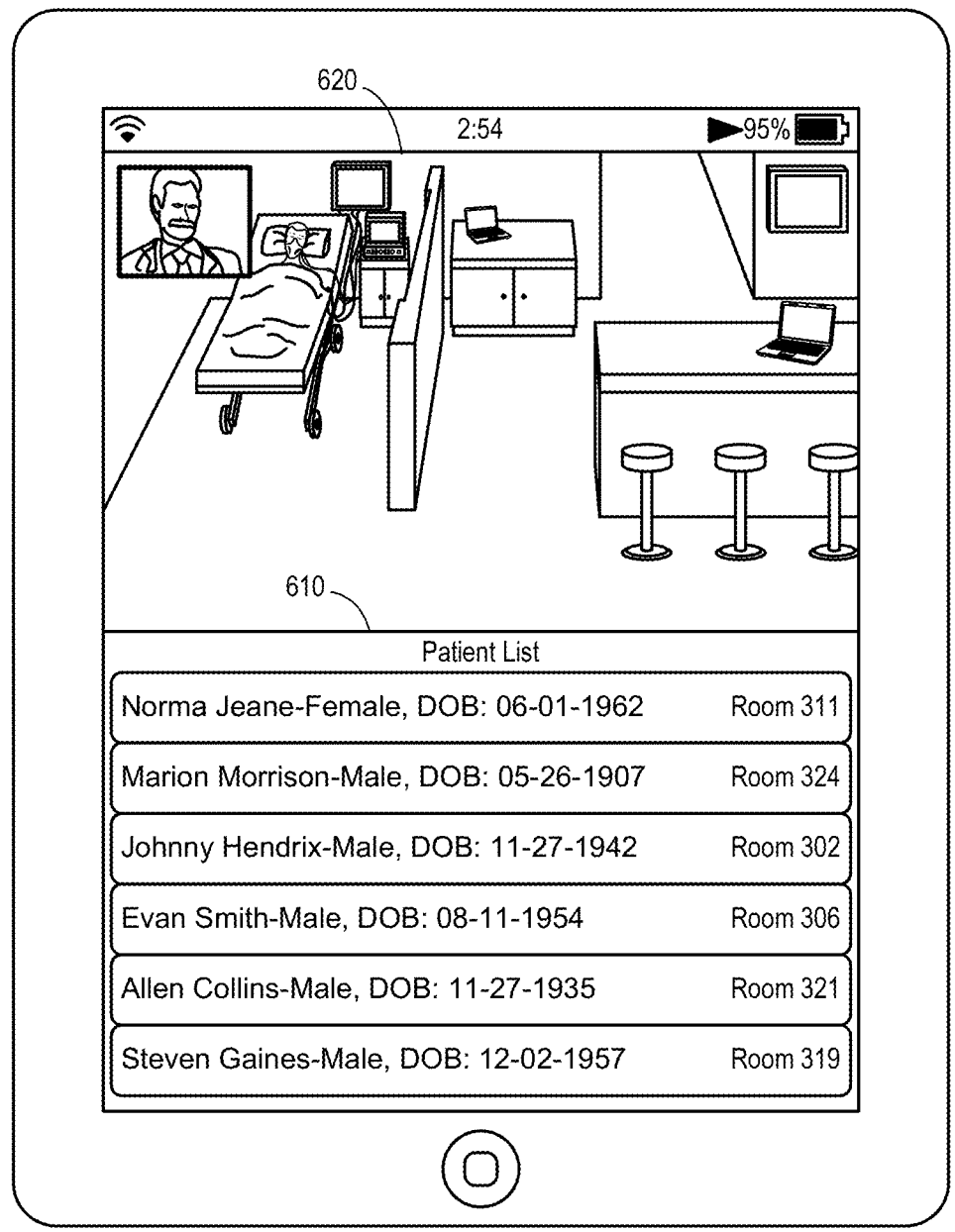
FIG. 6 illustrates a selectable destination patient list that can be used within an RPI to navigate a telepresence device.

FIG. 6 illustrates an embodiment 600 of an RPI with a panel 620 displaying a live feed from a telepresence device. A lower panel 610 may display a list of patients. A user may select a patient on the patient list to direct the telepresence device to navigate to the selected patient. Again, the telepresence device may be manually driven, autonomously navigate, or semi-autonomously navigate to the selected destination. The patient list may further include one or more meters or visual indicators indicating patient condition, criticality, or other current health metric associated with each patient. The list may further include a visual indicator of a distance or estimated travel time from the current position of the telemedicine device to the corresponding patient. These measures of patient condition and travel time may be combined to create a single metric that represents a best or most clinically effective next patient to visit. The patient list may be sortable and/or filterable, such that the order of patients is continuously updated based on these or other variables.

Figure 7:
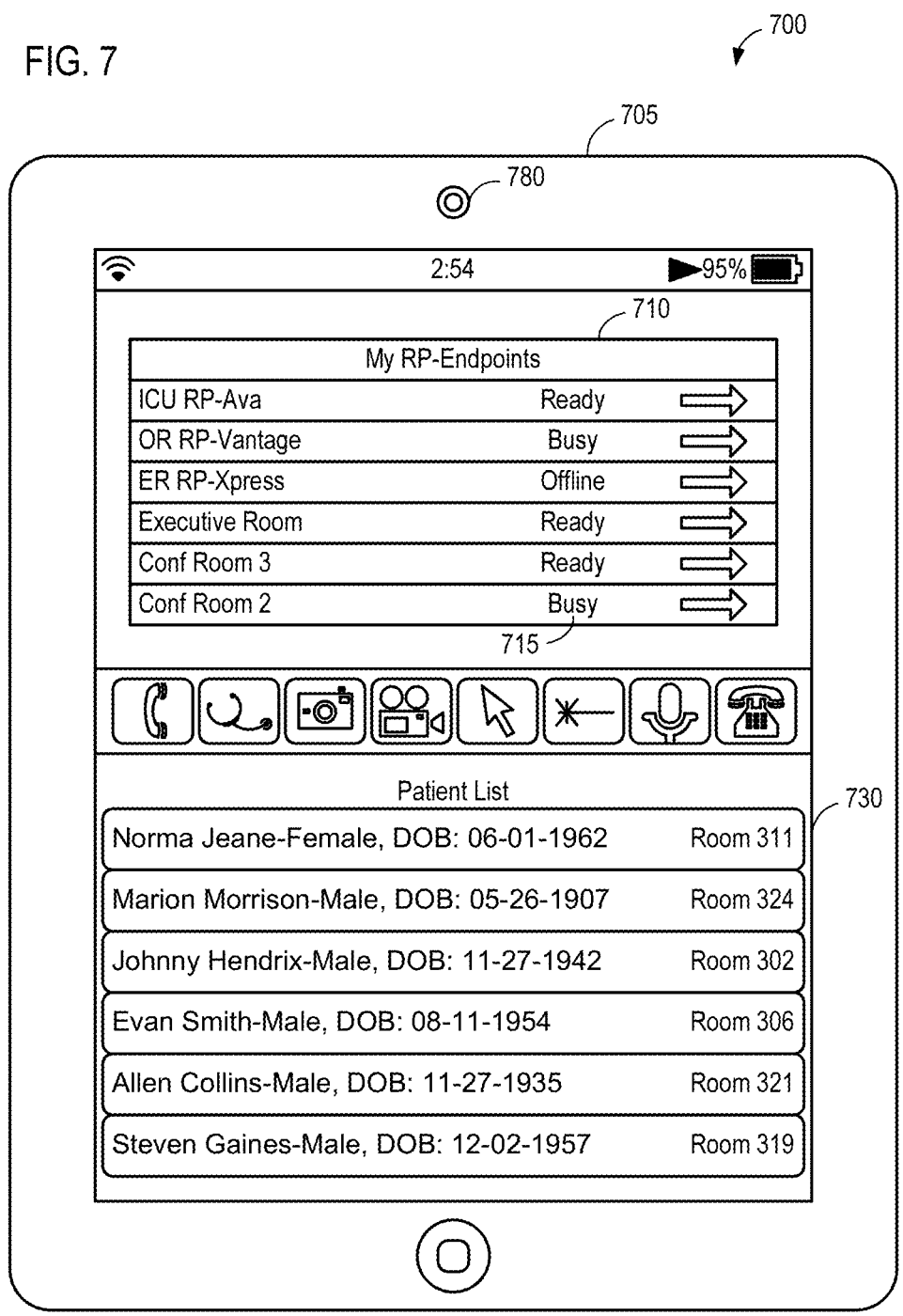
FIG. 7 illustrates a toolbar separating an endpoint list and a patient list in an RPI, allowing for quick user selection of various possible permutations.

FIG. 7 illustrates an embodiment 700 of an RPI on a RAD 705, including a video window 710 displaying a list of telepresence devices to which the user has access, a work space window 730 displaying a list of patients, and a toolbar 715 as a tool belt dividing the display. In various embodiments, the selection of a telepresence device via video window 710 will display a live video feed from the selected telepresence device and initiate a communication session with the telepresence device to allow the user of the RPI on the RAD 705 to control the telepresence device and/or join in a multi-user experience with the telepresence device. The selection of a patient via work space window 730 may automatically select an associated telepresence device based on availability, proximity, and/or other preferences. Alternatively, the user of the RPI on the RAD 705 may additionally select a telepresence device. The selection of a patient via work space window 730 may also direct a telepresence robot to navigate to the location of the patient.

Figure 8:
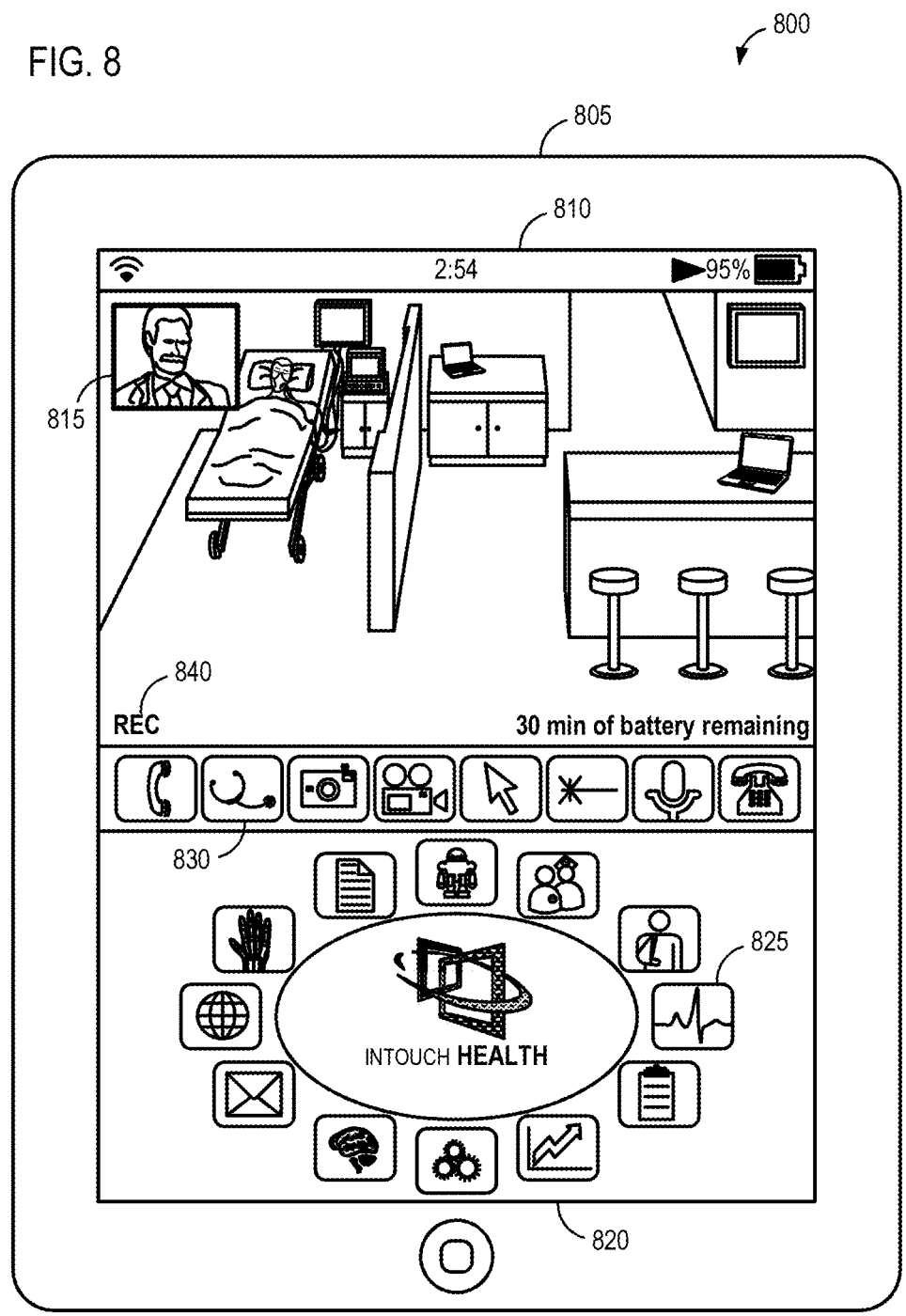
FIG. 8 illustrates a toolbar for managing modules and control operations available via an RPI, while simultaneously displaying a video feed from a telepresence device.

FIG. 8 illustrates an embodiment 800 of an RPI on a RAD 805, including a toolbar 825 in a lower panel 820. The toolbar may provide quick access to any of a wide variety of settings and/or features of the RPI. A user may select an icon using any of a wide variety of methods depending on the RAD 805. For instance, a user may touch an icon to select it. Settings and/or features of the RPI may be accessed simultaneously while a live video feed is shown in the upper panel 810. A media management toolbar 830 (selectively enabled) may allow for the video feed in upper panel 810 to be recorded, at 840. A notification 825 may alert a user of the RAD 805 that the battery on the telepresence device is nearly depleted. As in previous embodiments, a window 815 may display the image currently being captured by a camera on the RAD 805 or managing modules and control operations available via an RPI, while simultaneously displaying a video feed from a telepresence device.

According to various embodiments, the toolbar 825 may provide access to a handset, a stethoscope, a camera, a video, a live cursor, a laser pointer, microphone settings, a map, navigational options, a disconnect button, and/or other feature, option or settings. The toolbar 825 may provide access to various other functions or applications, such as StrokeRE- SPOND, SureNotes, a media manager, patient data, lab results, image data, and/or team communication.

Figure 9:
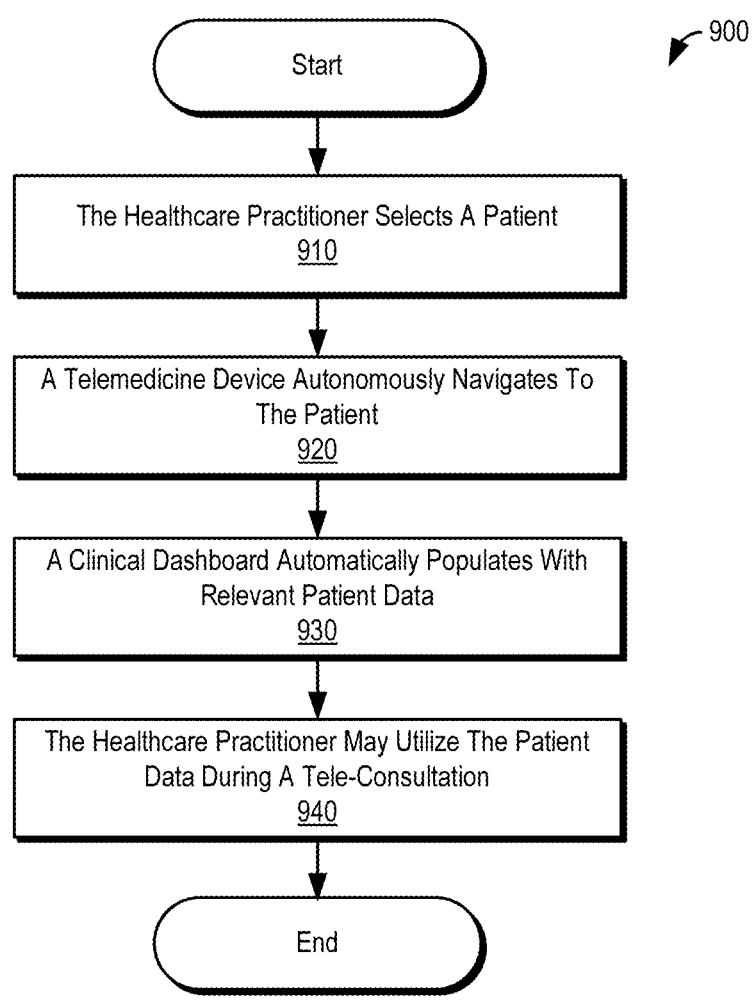
FIG. 9 illustrates a flow chart of a method for automatically populating a dashboard with relevant patient data when utilizing a telemedicine device.

FIG. 9 illustrates a flow chart of a method 900 for automatically populating a dashboard with relevant patient data when utilizing a telemedicine device. According to various embodiments, a healthcare practitioner may utilize a RAD configured with an RPI to monitor or communicate with a patient. The RPI may allow the healthcare practitioner to access a telepresence network configured with one or more telepresence devices, such as an autonomous telemedicine device. The healthcare practitioner may select a patient using the RPI, at 910. A telemedicine device associated with the RPI, the telepresence network, the healthcare practitioner, and/or the patient may autonomously navigate to the patient, at 920. The RPI may show an image of the patient captured by a camera of the telemedicine device, the RPI may show an image of the patient, monitors, charts, surroundings, etc.

During or prior to a tele-consultation with the patient, a clinical dashboard on the RPI may be automatically populated with relevant patient data, at 930. For example, panels on a display of the RAD may be populated with various statistics, charts, graphs, telemetry data, personal data, and other relevant data associated with the patient. The healthcare practitioner may utilize the patient data during the tele-consultation, at 940. The healthcare practitioner may make notes and/or update electronic medical records using the RPI. The telemedicine device may be configured to automatically record all or portions of the tele-consultation, relevant patient data gathered during the tele-consultation, and/or automatically update electronic medical records.

Figure 10:
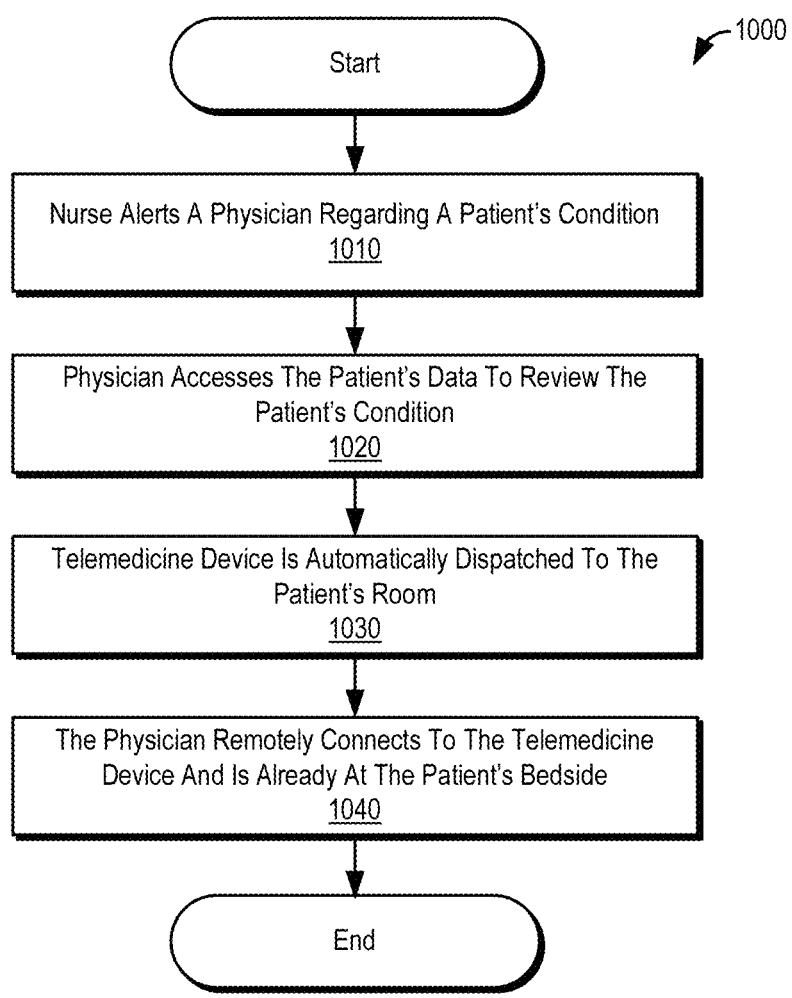
FIG. 10 illustrates a flow chart of a method for intelligently dispatching an autonomous telemedicine device.

FIG. 10 illustrates a flow chart of a method 1000 for intelligently dispatching an autonomous telemedicine device. A nurse may alert a physician regarding a patient's condition, at 1010. For example, a nurse may identify a symptom that requires urgent attention. A responding physician may access the patient's data to review the patient's condition, at 1020. A telepresence network and/or a telemedicine device may detect that a patient's data is being reviewed by the physician, and the telepresence device may be automatically dispatched to the patient's room, at 1030. The physician may remotely connect to the telemedicine device, such as via an RPI on a RAD, at 1040. Because the telepresence network and/or the telemedicine device detected the access to the patient's data, the telepresence device may already be at the patient's bedside or en route to the patient's bedside when the physician connects via the RPI.

Figure 11:
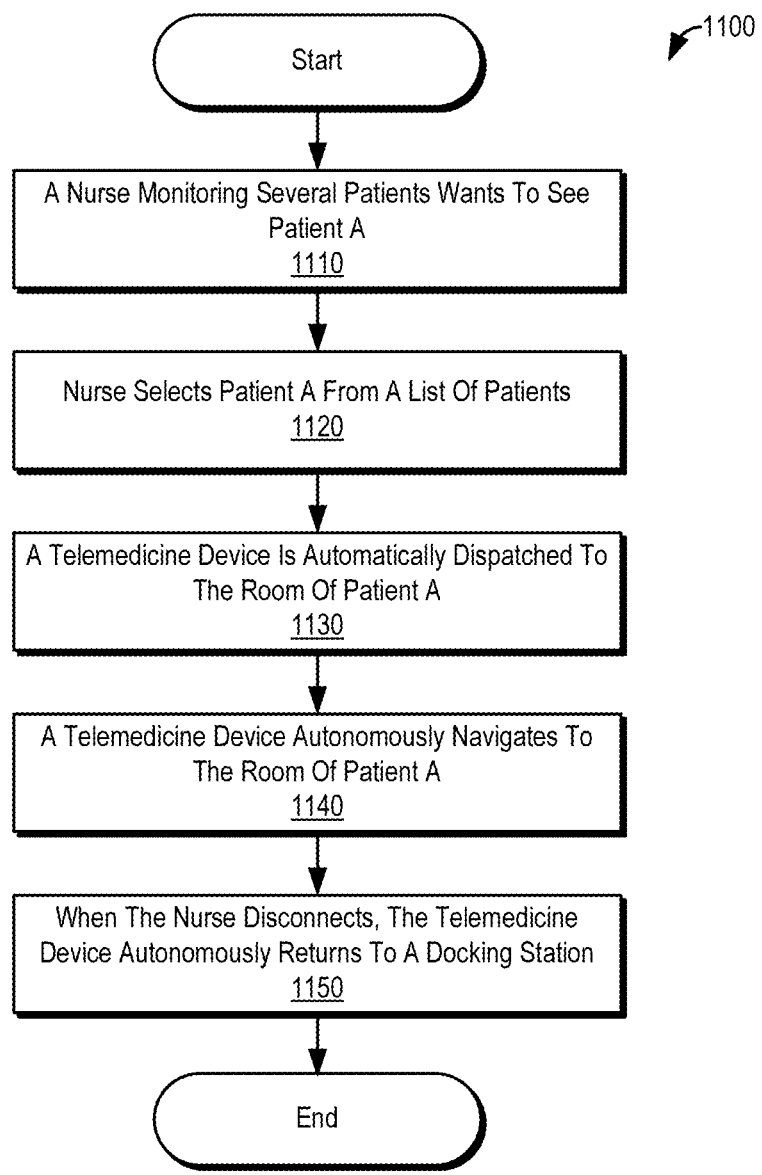
FIG. 11 illustrates a flow chart of another method for intelligently dispatching an autonomous telemedicine device.

FIG. 11 illustrates a flow chart of another method 1100 for intelligently dispatching an autonomous telemedicine device. A nurse may be assigned to monitor several patients (patients A-Z) and decide that he wants to see Patient A, at 1110. The nurse may select Patient A from a list of patients, at 1120. In some embodiments, the nurse may select Patient A via a display interface directly on a telemedicine device. In other embodiments, the nurse may select Patient A via an RPI on a RAD in communication with a telepresence network and/or the telemedicine device. In response to the nurse's selection of Patient A from the list of patients, a telemedicine device may be automatically dispatched to the room of patient A, at 1130. The telemedicine device may autonomously navigate to the room of patient A, at 1140. When the nurse disconnects, the telemedicine device may autonomously return to a docking station, at 1150.

Figure 12:
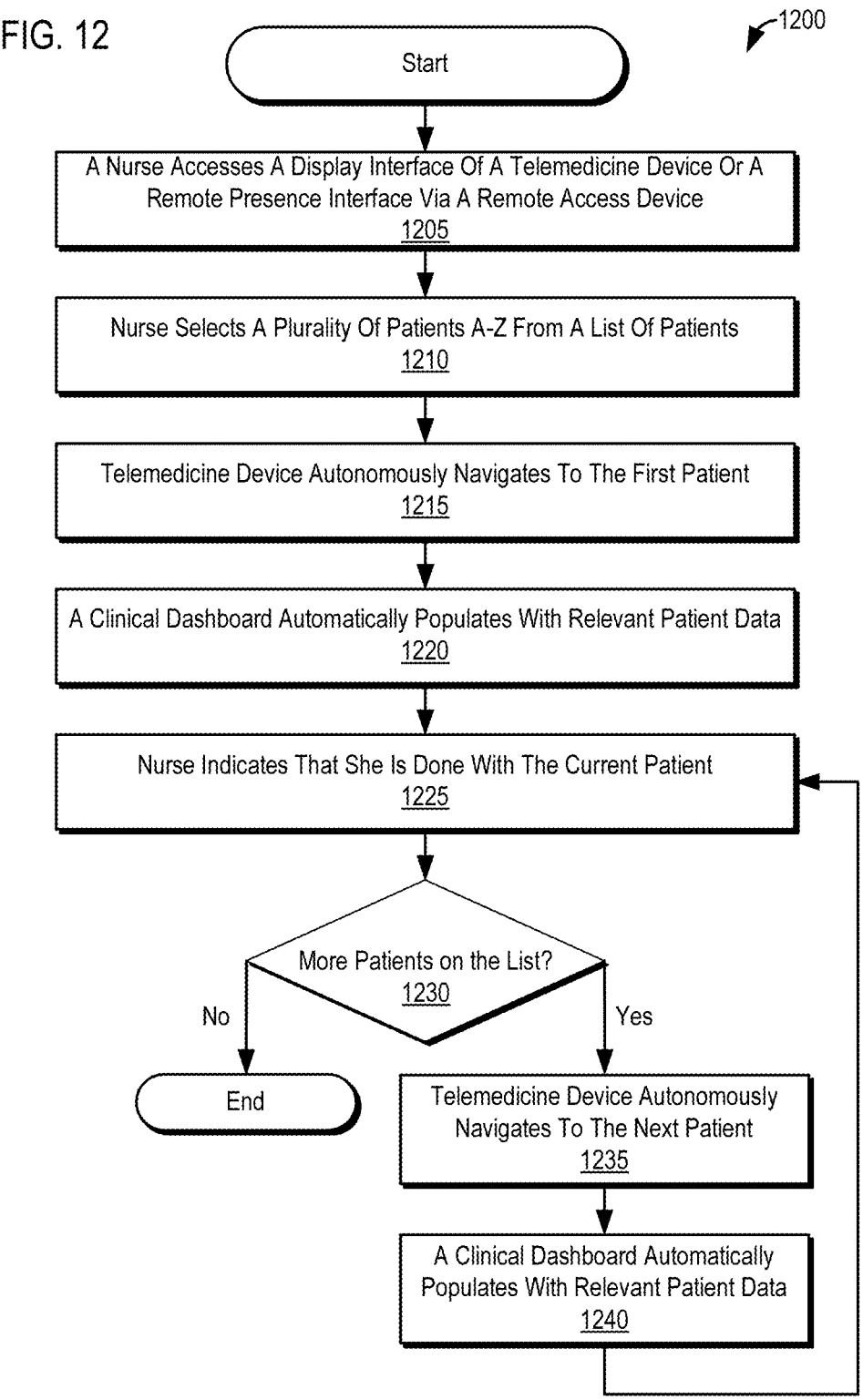
FIG. 12 illustrates a flow chart of a method for a nurse to attend rounds using a telemedicine device to sequentially visit a number of patients.

FIG. 12 illustrates a flow chart of a method 400 for a nurse to attend rounds using a telemedicine device to sequentially visit a number of patients. A nurse accesses a display interface of a telemedicine device or an RPI on a RAD, at 1205. The nurse selects a plurality of patients A-Z from a list of patients, at 1210. A telemedicine device autonomously navigates to the first patient, at 1215. A clinical dashboard on the RAD automatically populates with relevant patient data for the first patient, at 1220. In various embodiments, the RPI may allow the nurse to view and/or hear the patient, allow the patient to view and/or hear the nurse, allow the nurse to perform various medical tasks, such as check charts, monitors, medical instrument readouts, and/or perform various medical checkups. For example, the telemedicine device may be equipped with a stethoscope, heart rate monitor, blood pressure monitor, and/or other medical device. Such medical devices may be remotely useable via the RPI.

When finished with an individual patient, the nurse may indicate that she is done with the current patient via the RPI on the RAD, at 1225. For example, the nurse may select a next patient on a list of patients, or select a "next patient" button via the RPI. If there are more patients on the list of the plurality of patients selected by the nurse, at 1230, the telemedicine device may autonomously navigate to the next patient, at 1235. Again, a clinical dashboard on the RPI may automatically populate with relevant patient data, at 1240. Following the remote visit/consultation, the nurse may indicate that she is done with the current patient, at 1225. If there are more patients on the list, at 1230, then the telemedicine device may autonomously and/or automatically navigate to the next patient, at 1235. The cycle may continue until there are no more patients on the list, at 1230. At this point, the nurse has completed the rounds and the process may end. The telemedicine device may be configured to autonomously return to its dock.

According to various embodiments, the list of patients to be visited may be manually generated by a healthcare practitioner, or automatically generated by a scheduling system. Additionally, the order of the list may be continuously updated based on the condition of patients as they are visited during the rounds. For example, real-time data may indicate that a particular patient should be checked on more frequently. Accordingly, the list of patients and/or the order in which they are visited may be updated based on real-time patient conditions and/or other inputs provided by a healthcare practitioner. In some instances, a healthcare practitioner may indicate that a particular patient should be visited more often than the data would otherwise suggest. Additionally, the list of patients may be used to populate a queue of patients to be visited by remote healthcare practitioners when they log in to a telemedicine device. The queue may include numerous patients associated with one or more healthcare practitioners. The queue may be updated, filtered, and/or re-ordered based on the healthcare practitioner who logs in, the current status of the patients, and/or other relevant factors. In some embodiments the healthcare practitioner may manually override the automatically generated queue.

Figure 13:
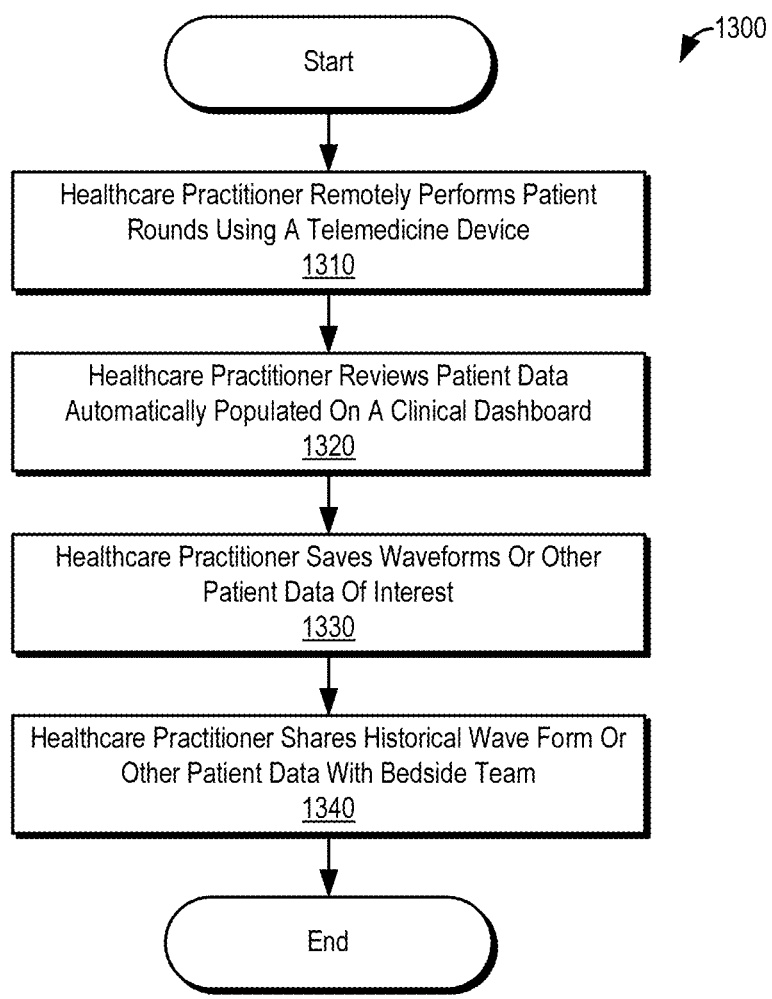
FIG. 13 illustrates a flow chart of a method for a healthcare practitioner to perform patient rounds using a telemedicine device while viewing, saving, and sharing relevant patient data.

FIG. 13 illustrates a flow chart of a method 1300 for a healthcare practitioner to perform patient rounds using a telemedicine device while viewing, saving, and sharing, relevant patient data. A healthcare practitioner remotely performs patient rounds using a telemedicine device, at 1310. For example, using the process described above with reference to FIG. 12. The healthcare practitioner may review patient data automatically populated on a clinical dashboard of an RPI while simultaneously participating in a telepresence session with the patient, at 1320. The healthcare practitioner may use a multimedia module of the RPI to save waveforms or other patient data of interest, at 1330. The healthcare practitioner may share on a display associated with the telemedicine device historical waveforms or other patient data with a bedside team directly via the RPI, via a multi-person telepresence session, and/or via access to a multimedia database, at 1340.

Figure 14:
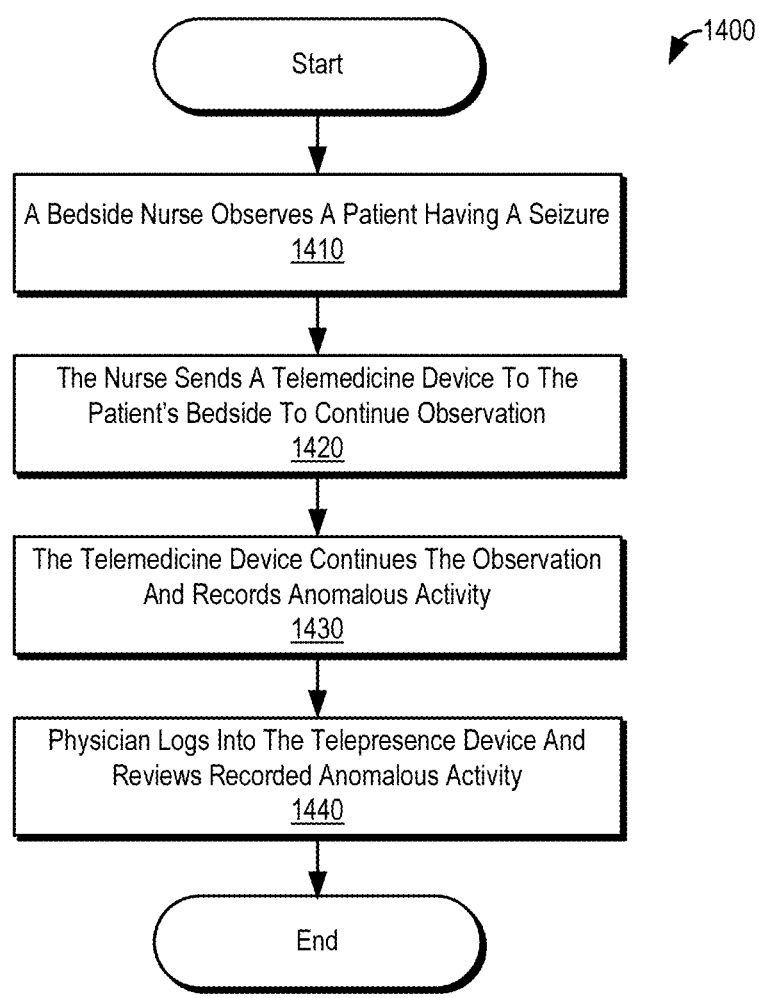
FIG. 14 illustrates a flow chart of a method for a nurse to send a telemedicine device to observe a patient for a period of time.

FIG. 14 illustrates a flow chart of a method 1400 for a nurse to send a telemedicine device to observe a patient for a period of time. A bedside nurse may observe a patient having a seizure, at 1410. The nurse sends a telemedicine device to the patient's bedside to continue observation, at 1420. The telemedicine device may continue the observation and may record all activity or anomalous activity, at 1430. The physician may log into the telepresence device and review recorded activity, at 1440.

Figure 15A:
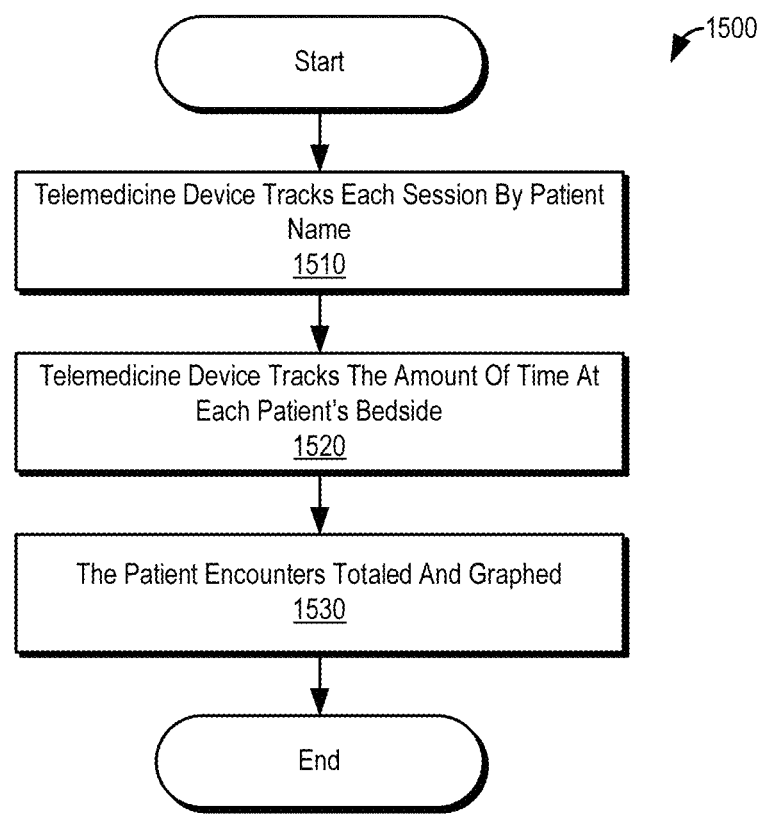
FIG. 15A illustrates a flow chart of a method for tracking the amount of time a telemedicine device spends with each patient.

FIG. 15A illustrates a flow chart of a method 1500 for tracking the amount of time a telemedicine device spends with each patient. The telemedicine device tracks each session and/or usage by patient name (or other identifying characteristic), at 1510. The telemedicine device may track the amount of time it spends at each patient's bedside, or is otherwise being used in conjunction with a particular patient, at 1520. Additionally, the telemedicine device may track the usage of one or more devices or functionalities associated with the telemedicine device, such as a camera, stethoscope, otoscope, auxiliary video port or other auxiliary input, privacy handset, or other feature or device associated with the telemedicine device. The telemedicine device, a telepresence system, and/or an RPI may total the patient encounters and present them, such as via a graph or data chart, at 1530.

Figure 15B:
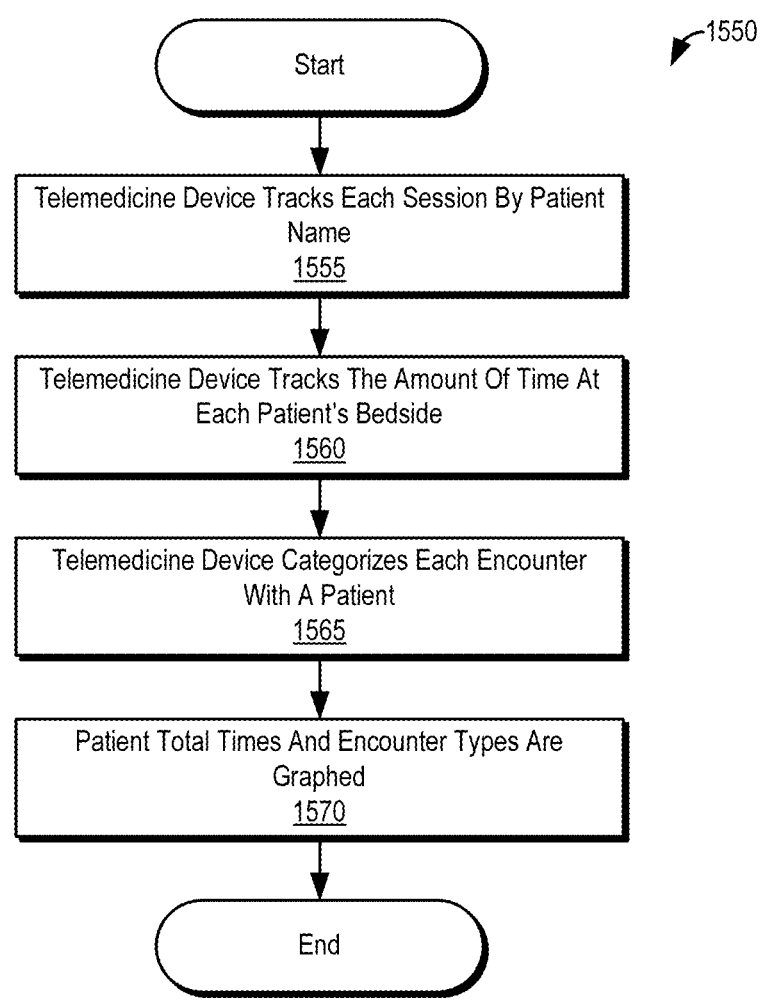
FIG. 15B illustrates a flow chart of a method for tracking the usage of a telemedicine device with respect to individual patients.

FIG. 15B illustrates a flow chart of a method 1550 for tracking the usage of a telemedicine device with respect to individual patients. The telemedicine device (or related system) may track each session by patient name or other identifying characteristic, at 1555. The telemedicine device may track the amount of time it spends at each patient's bedside, or otherwise being used in conjunction with a particular patient, at 1560. The telemedicine device may categorize each encounter with a patient, at 1565. For example, each encounter may be categorized by type of visit, the type of person making the visit, the outcome of the visit, the reason for the visit, or other characteristic of the visit. The telemedicine device, a telepresence system, and/or an RPI may total the patient encounters and present them, such as via a graph or data chart, at 1570.

Figure 16:
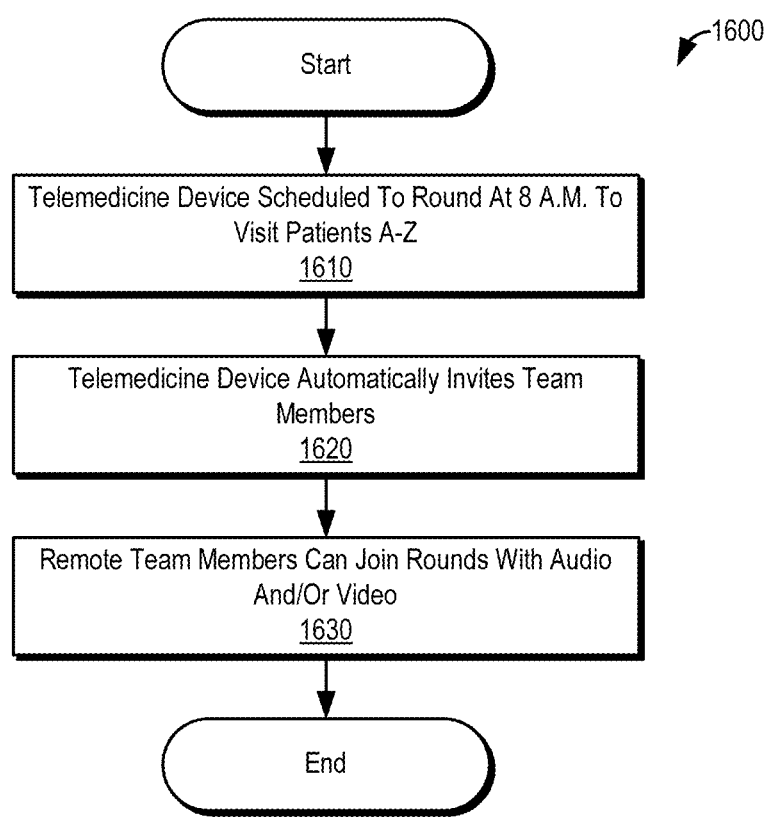
FIG. 16 illustrates a flow chart of a method for an autonomous telemedicine device to invite healthcare practitioners while it automatically performs patient rounds.

FIG. 16 illustrates a flow chart of a method 1600 for an autonomous telemedicine device to invite healthcare practitioners while it automatically performs patient rounds. The telemedicine device may be scheduled to visit patients A-Z at 8 a.m., at 1610. The telemedicine device may automatically invite team members to participate, via a telepresence session, as the telemedicine device performs rounds, at 1620. The remote team members may join in the rounds via an RPI on a RAD, at 1630.

Additionally, an autonomous telemedicine device may be configured to perform, for example, compliance rounds. The telemedicine device may be configured to review patient orders for each of a plurality of patients and then visit each patient and check for compliance. For example, a patient may have orders pertaining to a change of bed elevation, DVT prophylaxis (compression sleeves around a portion of a patient's leg), a medication, confinement to bed, and/or other doctor-ordered condition. The telemedicine device may then navigate to each patient and using, for example, image analysis, computer vision techniques, and/or data monitoring devices, check for patient compliance. In some embodiments, the telemedicine device may navigate to each patient's bedside and then call a healthcare practitioner and invite the healthcare practitioner to confirm, via a teleconference, that the patient has complied with a set of orders. In some embodiments, the telemedicine device may be configured to question associated healthcare practitioners and/or the patient to ask about compliance. For example, the telemedicine device may simply verify that each patient is "doing OK," still in bed, and/or asleep.

Figure 17:
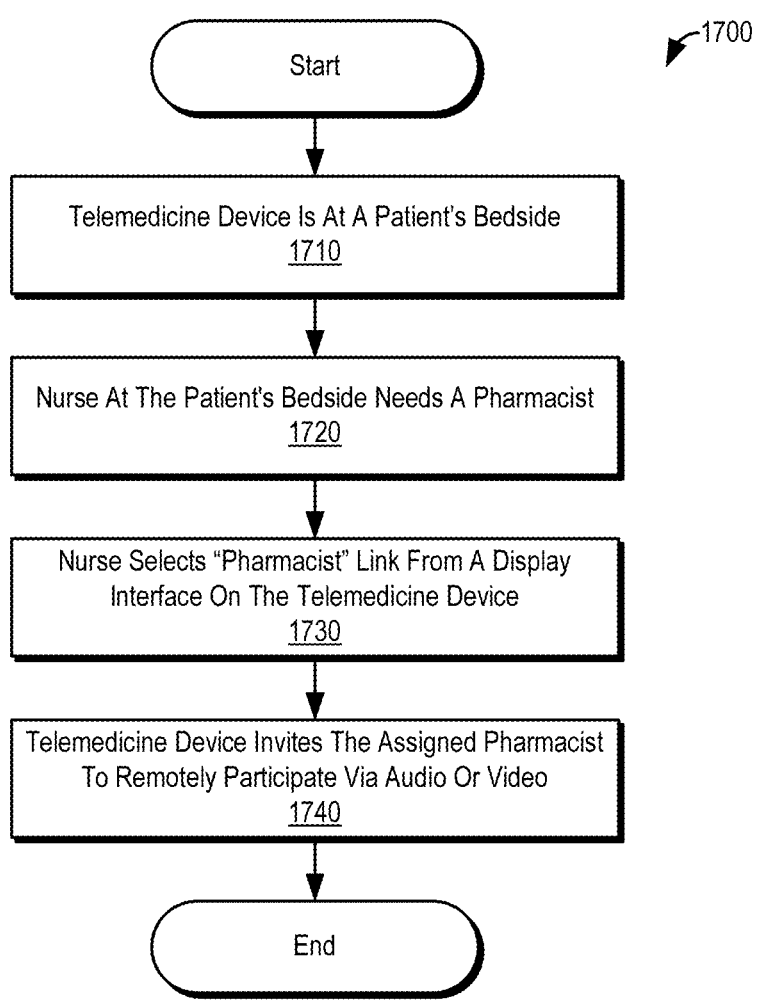
FIG. 17 illustrates a flow chart of a method for a telemedicine device to intelligently facilitate remote telepresence connections.

FIG. 17 illustrates a flow chart of a method 1700 for a telemedicine device to intelligently facilitate remote telepresence connections. The telemedicine device may be at a patient's bedside, at 1710. A nurse, also at the patient's bedside, may need assistance from another health professional, for example, a pharmacist, at 1720. The nurse may select a "pharmacist" link from a display interface on the telemedicine device or via an RPI on a RAD, at 1730. According to various embodiments, the nurse may not need to specify a particular pharmacist. The telemedicine device may invite the assigned pharmacist to remotely participate via a telepresence session, at 1740. For example, a pharmacist assigned to the patient, a pharmacist who last administered to the patient, the nearest pharmacist, an available pharmacist, an on-call pharmacist, and/or other available pharmacist may be automatically invited by the telemedicine device or an associated telepresence system. In various embodiments, the invitation may be sent via email, text message, personal message, voice message, a system alert to a RAD, a proprietary messaging system, or the like.

In alternative embodiments, any of a patient, nurse, physician, doctor, visitor, remote user, healthcare practitioner, and/or other person may make a general request for a different patient, nurse, physician, doctor, visitor, remote user, healthcare practitioner, and/or other person. The telemedicine device, a telepresence system, and/or an RPI may receive the general request and make a context-based specific request. For example, a patient may request a consultation with a "doctor" via a display interface of a telemedicine device. The telemedicine device may, based on the context of the location, patient, time, and/or other factors, send a request to a specific doctor to participate in a telepresence session via the telemedicine device. The doctor may utilize an RPI on a RAD to remotely log in to the telemedicine device.

Figure 18:
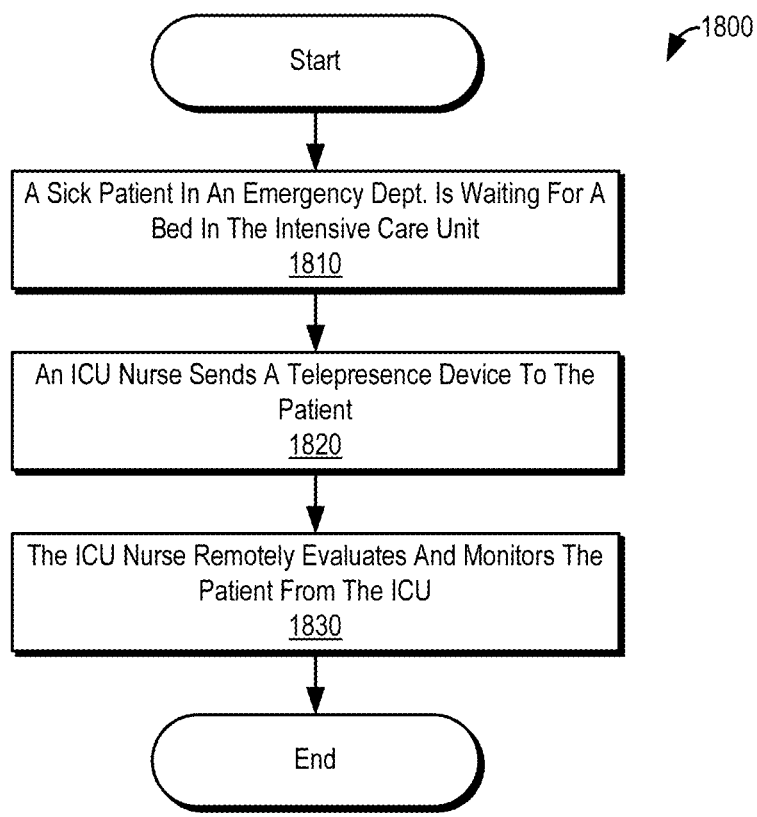
FIG. 18 illustrates a flow chart of a method for using a telemedicine device to evaluate and/or monitor a remote patient.

FIG. 18 illustrates a flow chart of a method 1800 for using a telemedicine device to evaluate and/or monitor a remote patient. For example, a sick patient in an emergency department may be waiting for a bed and/or room in an intensive care unit (ICU), at 1810. An ICU nurse may send a telemedicine device to the patient, at 1820. The ICU nurse may remotely evaluate and monitor the patient from the ICU ward, at 1830. Accordingly, a patient needing the expert care of an ICU nurse may receive it remotely via the telemedicine device.

Figure 19:
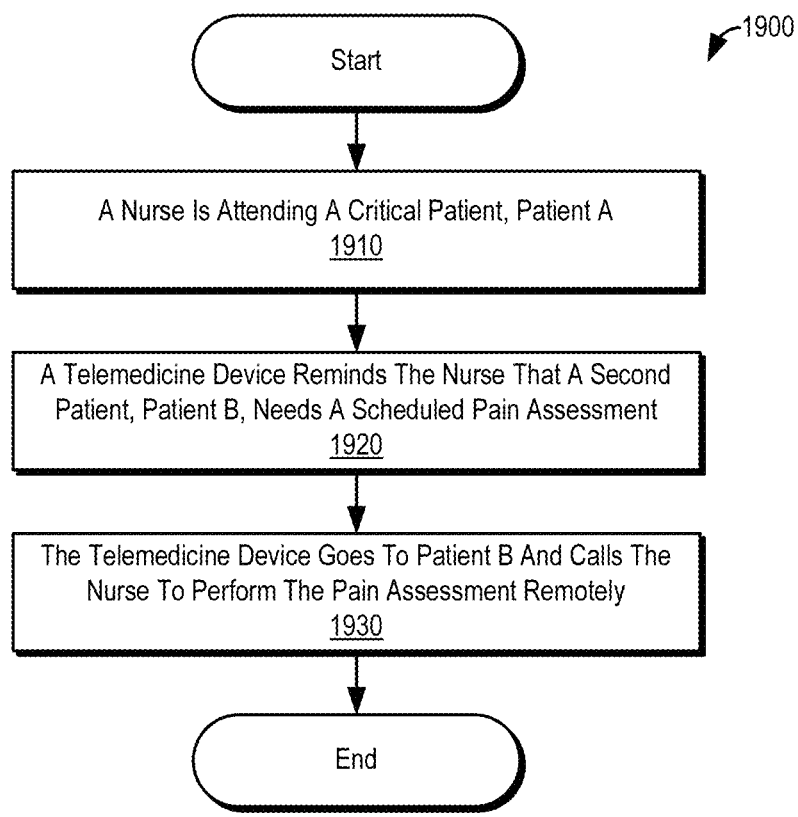
FIG. 19 illustrates a flow chart of a method for using a telemedicine device as a reminder service in conjunction with remote telepresence consultations.

FIG. 19 illustrates a flow chart of a method 1900 for using a telemedicine device as a reminder service in conjunction with remote telepresence consultations. In the illustrated example, a nurse may be attending a critical patient, Patient A, at 1910. A telemedicine device may remind the nurse that a second patient, Patient B, needs a scheduled pain assessment, at 1920. The nurse may elect to remain with Patient A while dispatching the telemedicine device to Patient B. The telemedicine device may autonomously navigate to Patient B and call the nurse to perform the pain assessment remotely, at 1930. The nurse may utilize an RPI on a RAD to remotely perform the pain assessment in a telepresence session.

Figure 20:
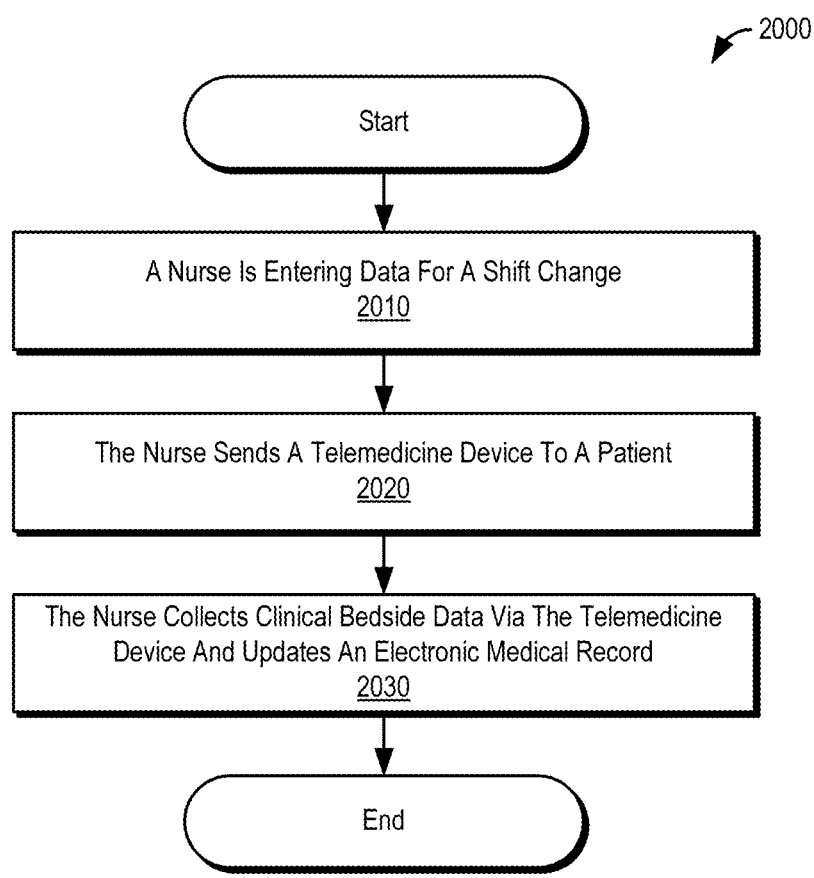
FIG. 20 illustrates a flow chart of a method for utilizing a telemedicine device to update electronic medical records.

FIG. 20 illustrates a flow chart of a method 2000 for utilizing a telemedicine device to update electronic medical records. In various situations a medical professional has reason to update a patient's medical record. For example, prior to a shift change, a nurse typically updates each patient's medical record. In the illustrated embodiment, a nurse is entering data for a shift change, at 2010. The nurse sends a telemedicine device to a patient, at 2020. The nurse collects clinical bedside data via the telemedicine device and updates an electronic medical record, at 2030. In one embodiment, the telemedicine device may be configured to communicate with an electronic medical record database to automatically (or via manual instructions) update an electronic medical record via the telemedicine device and/or via an RPI on a RAD.

Figure 21:
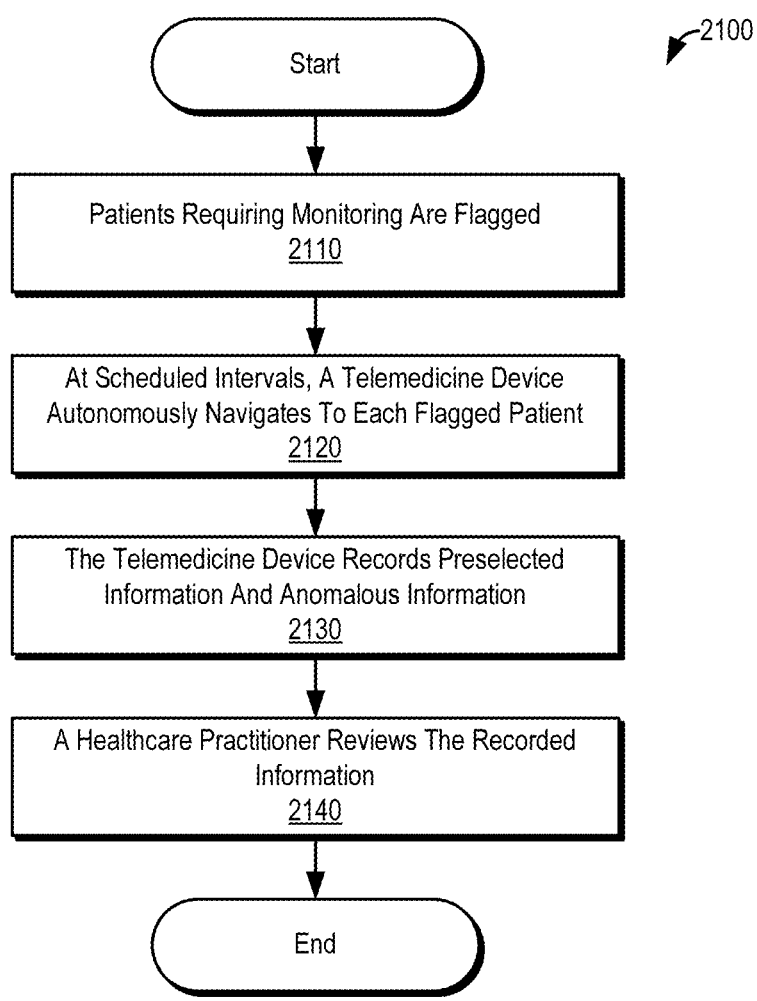
FIG. 21 illustrates a flow chart of a method for utilizing an autonomous telemedicine device to check on patients and record preselected and/or anomalous conditions.

FIG. 21 illustrates a flow chart of a method 2100 for utilizing an autonomous telemedicine device to check on patients and record preselected and/or anomalous conditions. A healthcare practitioner may flag patients requiring monitoring, at 2110. At scheduled intervals (automatically determined or as scheduled by the healthcare practitioner), a telemedicine device may autonomously navigate to each flagged patient, at 2120. The telemedicine device may record preselected information and/or anomalous information, at 2130. Information may be determined anomalous if it deviates from a specified threshold level, for example. A healthcare practitioner may then review the recorded information, at 2140. For example, a healthcare practitioner may flag patients for visits during the night and then review any specific or anomalous information recorded by the telemedicine device.

Figure 22:
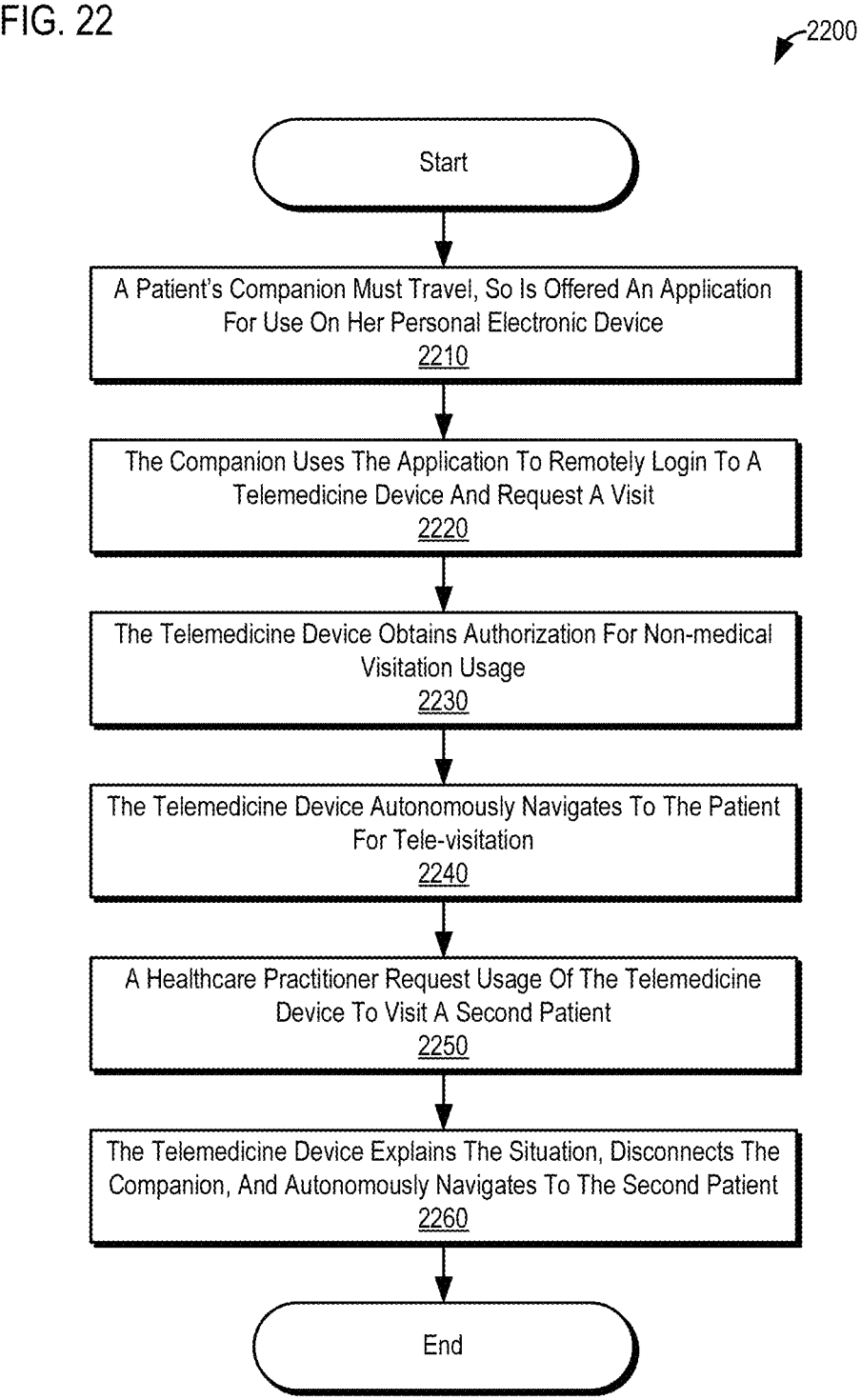
FIG. 22 illustrates a flow chart of a method for utilizing an autonomous telemedicine device to allow a companion of a patient to perform remote visits.

FIG. 22 illustrates a flow chart of a method 2200 for utilizing an autonomous telemedicine device to allow a companion of a patient to perform remote visits. In the illustrated embodiment, a patient's companion (e.g., spouse, friend, family member, domestic partner) must travel, so is offered an application for use on a personal electronic device, at 2210. The companion uses the application to remotely log in to a telemedicine device and request a visit with the patient, at 2220. The telemedicine device obtains authorization for non-medical visitation usage, at 2230. For example, non-medical visitations may be given a lower priority than actual medical usages. In some embodiments, a healthcare facility may include telemedicine devices specifically dedicated to non-medical visits. Such telemedicine devices may not have all the same features of telemedicine devices for use by healthcare practitioners.

Alternatively, a telemedicine device may selectively disable specific features when a user logs in as a companion. For example, live audio and video may be disabled while the telemedicine navigates through a healthcare facility. The live audio and/or video may then be enabled when the device reaches the target patient or other location where the privacy of the target patient, his or her companion, and other patients and staff in the facility can be reasonably assured. Additionally, the RPI of the companion may completely or partially prevent the companion from manually navigating the telepresence device. For example, the companion may have the ability to move the telepresence device about a particular room or within a specified radius of a bed of the target patient, but may not have the ability to move the device beyond some defined boundary. As another example, the companion may have the ability to control head movements and/or the direction a camera is aimed or zoomed, but not be able to control the movement of a base of a telemedicine device.

In some embodiments, the telemedicine device may limit the pan, tilt, or zoom range of a camera associated with the telemedicine device, to prevent other patients or staff from coming within the field of view of the camera. This limited range may be fixed or predetermined, may depend on scene analysis using image analysis techniques, and/or may be determined based on a calculation of the field of view of the camera associated with the telemedicine device as compared to items tagged in a map of the telemedicine device, such as patients, beds, or zones or regions designated as allowed or prohibited. The calculation of the field of view of the camera may depend on the location and pose of the telemedicine device, as well as pan, tilt, and zoom parameters of the camera associated with the telemedicine device.

Assuming permission is granted, the telemedicine device autonomously navigates to the patient for tele-visitation, at 2240. During the companion's telepresence session, a healthcare practitioner may request usage of the telemedicine device to visit a second patient for medical purposes, at 2250. The telemedicine device may explain the situation to the first patient and/or the companion, disconnect the companion, and autonomously navigate to the second patient, at 2260.

Variations may be made to the details of the above-described embodiments without departing from the underlying principles and scope of the present disclosure. Accordingly, the scope of the presently described systems and methods should be determined only by the following claims.

What is claimed:

1. A non-transitory computer-readable medium comprising program code that, when executed by a processor, performs a method for providing a remote telepresence patient visitation, the method comprising:
displaying a list of patients on a remote presence interface of a remote access device;
receiving a request from a user via the remote presence interface for a telepresence sessions with a selection of a plurality of patients from the list of patients;
directing a mobile telemedicine device to autonomously navigate to a first patient of the plurality of patients;
receiving patient data regarding the first patient from a patient data monitoring system;
populating a dashboard of the remote presence interface with the patient data related to the first patient, such that the patient data is viewable during a telepresence session;
in response to the telemedicine device reaching the first patient, initiating the telepresence session between the user and the first patient via the remote presence interface on the remote access device;
receiving, subsequent to initiating the telepresence session with the first patient, an indication that the user wishes to conclude the telepresence session with the first patient; and
directing, upon conclusion of the telepresence session with the first patient, the telemedicine device to autonomously navigate to a second patient of the plurality of patients.

2. The non-transitory computer-readable medium of claim 1, further comprising:
in response to real-time data concerning a condition of a third patient, automatically directing the telemedicine device to the third patient before the second patient.

3. The non-transitory computer-readable medium of claim 1, further comprising:
in response in response to patient data of a third patient triggering an alarm condition:

automatically dispatching the telemedicine device to the third patient; and
sending an invitation to a medical practitioner to begin a telepresence session with the third patient.

4. The non-transitory computer-readable medium of claim 1, where directing comprises:
in response to detecting that the patient data of the first patient is being reviewed, automatically dispatching the telemedicine device to a location of the first patient.

5. The non-transitory computer-readable medium of claim 4, further comprising:
continuously updating an order of patients for the telemedicine device to visit based on real-time data relating to conditions of each of a plurality of patients.

6. The non-transitory computer-readable medium of claim 1, wherein the patient data comprise at least one of vital signs, a waveform, and biometric data.

7. The non-transitory computer-readable medium of claim 1, further comprising:
receiving an indication that the user wishes to conclude the telepresence session; and
directing the telemedicine device to autonomously navigate to a docking station.

8. The non-transitory computer-readable medium of claim 1, further comprising:
gathering patient data relating to the first patient; and
transmitting the patient data from the telemedicine device to the remote access device to be used in populating a remote dashboard of the remote presence interface on the remote access device, such that the patient data is viewable during the telepresence session.

9. The non-transitory computer-readable medium of claim 6, further comprising:
overriding an automatically-generated order for visiting one or more patients in response to a manual input.

10. The non-transitory computer-readable medium of claim 1, wherein the dashboard is populated with patient data before the telepresence session.

11. The non-transitory computer-readable medium of claim 1, further comprising:
sharing the patient data from the remote access device to a display associated with the telemedicine device viewable by a person in proximity to a bedside of the first patient.

12. The non-transitory computer-readable medium of claim 1, further comprising:
tracking an amount of time the telemedicine device is used in conjunction with a particular patient.

13. The non-transitory computer-readable medium of claim 1, further comprising:
displaying statistics on the remote presence interface relating to one or more encounters with the first patient.

14. The non-transitory computer-readable medium of claim 1, further comprising:
documenting an encounter of the telemedicine device with a particular patient, wherein documenting comprises categorizing the encounter by at least one of type of visit, a type of person making the visit, an outcome of the visit, and a reason for the visit.

15. A method comprising:
displaying a list of patients on a remote presence interface of a remote access device;
receiving a request from a user via the remote presence interface for a telepresence sessions with a selection of a plurality of patients from the list of patients;
directing a mobile telemedicine device to autonomously navigate to a first patient of the plurality of patients;
receiving patient data regarding the first patient from a patient data monitoring system;
populating a dashboard of the remote presence interface with the patient data related to the first patient, such that the patient data is viewable during a telepresence session;
in response to the telemedicine device reaching the first patient, initiating the telepresence session between the user and the first patient via the remote presence interface on the remote access device;
receiving, subsequent to initiating the telepresence session with the first patient, an indication that the user wishes to conclude the telepresence session with the first patient; and
directing, upon conclusion of the telepresence session with the first patient, the telemedicine device to autonomously navigate to a second patient of the plurality of patients.

16. The method of claim 15, further comprising:
storing a record of each of a plurality of patient visits in a memory of a telepresence robot, wherein each patient is identified by a unique identifier and the record includes:
an amount of time spent at each patient's bedside;
a category for each encounter with a patient;
usage information for a component of the telemedicine device; and
exporting the record.

17. The method of claim 15, further comprising:
receiving an instruction by the telemedicine device to autonomously navigate to each of a plurality of patients starting at a specified time; and
for each patient of the plurality of patients:
navigating the telemedicine device autonomously to the first patient;
inviting a user to join a telepresence session; and
transmitting audio, video, and/or patient data to the user via the telepresence session.

18. The method of claim 15, further comprising:
receiving an indication by the telemedicine device that a medical professional is needed to visit the first patient;
transmitting an invitation by the telemedicine device to the medical professional to join a telepresence session regarding the first patient; and
transmitting audio, video, and/or patient data to a remote access device to be viewed by the medical professional.

19. The method of claim 15, further comprising:
receiving at the telemedicine device an indication that a medical professional is needed to visit the first patient;
displaying a list of available medical professionals; and
transmitting, by the telemedicine device, an invitation to a selected medical professional to join the telepresence session.

20. The method of claim 15, further comprising:
transmitting, by the telemedicine device, an invitation to a user to join a telepresence session; and
transmitting audio, video, and/or patient data to the user via the telepresence session.

* * * * *